United States Patent [19]

Palmaz

[11] Patent Number: 4,739,762
[45] Date of Patent: Apr. 26, 1988

[54] EXPANDABLE INTRALUMINAL GRAFT, AND METHOD AND APPARATUS FOR IMPLANTING AN EXPANDABLE INTRALUMINAL GRAFT

[75] Inventor: Julio C. Palmaz, San Antonio, Tex.

[73] Assignee: Expandable Grafts Partnership, San Antonio, Tex.

[21] Appl. No.: 923,798

[22] Filed: Nov. 3, 1986

Related U.S. Application Data

[63] Continuation-in-part of Ser. No. 796,009, Nov. 7, 1985.

[51] Int. Cl.$^4$ ............................................. A61M 29/00
[52] U.S. Cl. .................................... 128/343; 604/104; 604/96; 623/1
[58] Field of Search ...................... 604/93, 49, 343, 97; 623/2; 128/344, 343, 1 R

[56] References Cited

U.S. PATENT DOCUMENTS

| | | | |
|---|---|---|---|
| 3,774,596 | 11/1973 | Cook | 604/266 |
| 3,868,956 | 3/1975 | Alfidi et al. | 604/266 |
| 3,882,845 | 5/1975 | Bucalo | 128/1 R |
| 3,889,685 | 6/1975 | Miller et al. | 128/348 |
| 4,140,126 | 2/1979 | Choudhury | 604/266 |
| 4,141,364 | 2/1979 | Schultze | 604/266 |
| 4,183,102 | 1/1980 | Guiset | 3/1.4 |
| 4,299,226 | 11/1981 | Banka | 604/266 |
| 4,318,410 | 3/1982 | Chin . | |
| 4,416,028 | 11/1983 | Erikson et al. | 604/266 |
| 4,425,908 | 1/1984 | Simon . | |
| 4,483,339 | 11/1984 | Gillis . | |
| 4,483,340 | 11/1984 | Fogarty et al. | 128/344 |
| 4,503,569 | 3/1985 | Dotter | 3/1.4 |
| 4,512,338 | 4/1985 | Balko . | |
| 4,553,545 | 11/1985 | Maass . | |
| 4,560,374 | 12/1985 | Hammerslag | 604/49 |
| 4,562,596 | 1/1986 | Kornberg | 604/266 |
| 4,564,014 | 1/1986 | Fogerty et al. . | |
| 4,577,631 | 3/1986 | Kreamer | 128/334 R |
| 4,580,568 | 4/1986 | Gianturco | 604/266 |
| 4,619,261 | 10/1986 | Guerriero | 604/97 |
| 4,650,466 | 3/1987 | Luther | 604/266 |

FOREIGN PATENT DOCUMENTS

| | | | |
|---|---|---|---|
| 0483372 | 4/1986 | European Pat. Off. . | |
| 1205743 | 9/1970 | United Kingdom | 128/343 |
| 2135585 | 9/1984 | United Kingdom . | |

OTHER PUBLICATIONS

"Flexible Balloon-Expanded Stent for Small Vessels-Work in Progress", Duprat et al., Radiology, Jan 1987, vol. 162, No. 1, pp. 276-278.
"Expandable Intraluminal Graft: A Preliminary Study"; Radiology, Jul. 1985; Paper Presented at 70th Scientific Assembly and Annual Meeting of the Radiological Society of North America, Nov. 25, 1984 by Julio C. Palmaz et al.
"Percutaneous Endovascular Stents: An Experimental Evaluation"; Wright et al., Radiology 156; 1985.
"Transluminal Expandable Nitinol Coil Stent Grafting: Preliminary Report Dotter et al.; Radiology 147; 1983.
"Non Surgical Placement of Arterial Endoprostheses: A New Technique Using Nitinol Wire"; Cragg et al., Radiology 147, 1983.
"Transluminally-Placed Coilspring Endurterial Tube Grafts"; Dotter Investigative Radiology; Sep.-Oct. 1969.
"Radiological Follow-Up of Transluminally Inserted Vascular Endoprostheses: An Experimental Study Using Expanding Spirals"; Radiology 152; 1984.

*Primary Examiner*—C. Fred Rosenbaum
*Assistant Examiner*—Gene B. Kartchner
*Attorney, Agent, or Firm*—Ben D. Tobor

[57] ABSTRACT

An expandable and deformable intraluminal vascular graft is expanded within a blood vessel by an angioplasty balloon associated with a catheter to dilate and expand the lumen of a blood vessel. The graft may be a thin-walled tubular member having a plurality of slots disposed substantially parallel to the longitudinal axis of the tubular member.

43 Claims, 2 Drawing Sheets

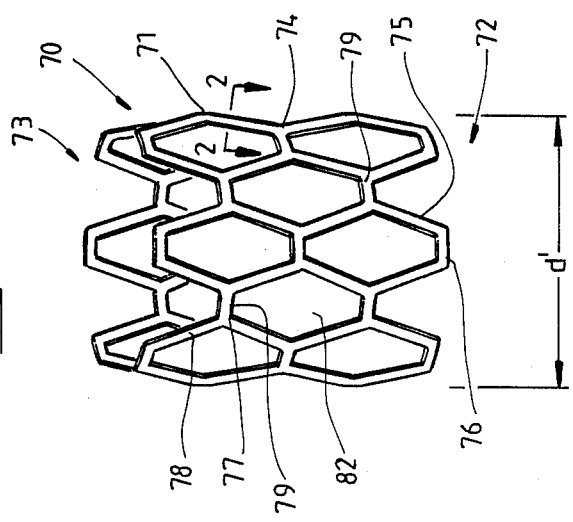
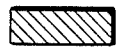
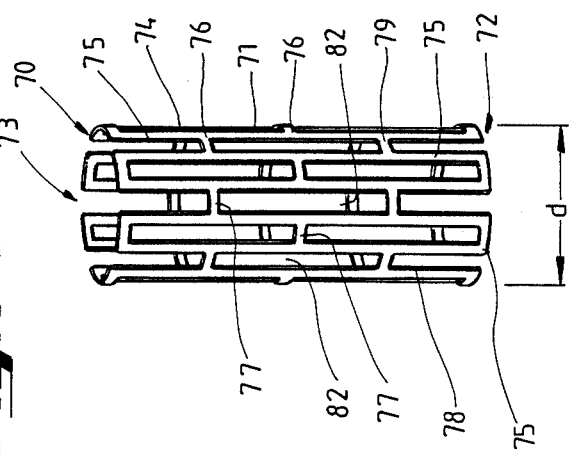

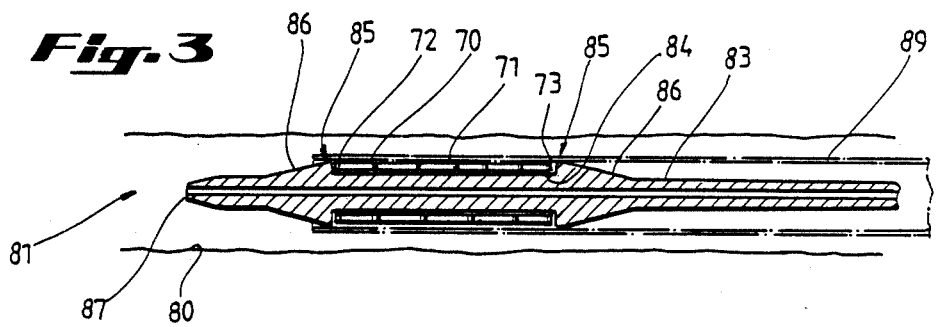
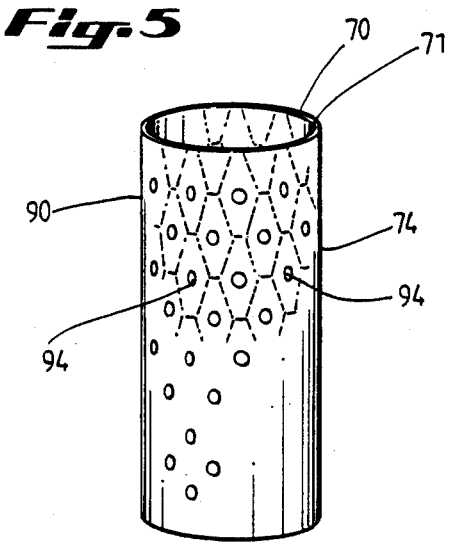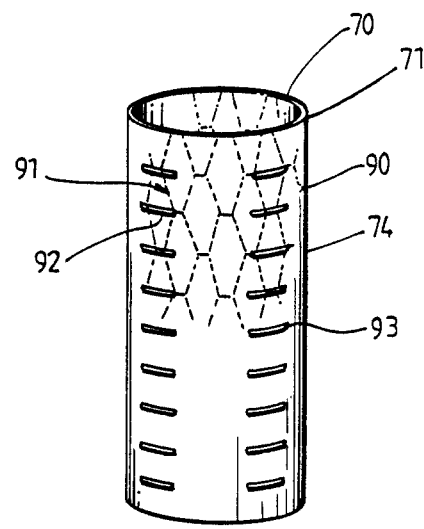

EXPANDABLE INTRALUMINAL GRAFT, AND METHOD AND APPARATUS FOR IMPLANTING AN EXPANDABLE INTRALUMINAL GRAFT

The government of the United States of America retains a non-exclusive, irrevocable, royalty-free license in this invention for all governmental purposes, pursuant to 37 C.F.R. § 100.6(b)(2).

RELATED APPLICATION

This application is a continuation-in-part of Applicant's co-pending application Ser. No. 06/796,009 filed Nov. 7, 1985 entitled Expandable Intraluminal Graft, and Method and Apparatus for Implanting an Expandable Intraluminal Graft.

FIELD OF THE INVENTION

The invention relates to an expandable intraluminal graft for use within a body passageway or duct and, more particularly, expandable intraluminal vascular grafts which are particularly useful for repairing blood vessels narrowed or occluded by disease; and a method and apparatus for implanting expandable intraluminal grafts.

DESCRIPTION OF THE PRIOR ART.

Intraluminal endovascular grafting has been demonstrated by experimentation to present a possible alternative to conventional vascular surgery. Intraluminal endovascular grafting involves the percutaneous insertion into a blood vessel of a tubular prosthetic graft and its delivery via a catheter to the desired location within the vascular system. Advantages of this method over conventional vascular surgery include obviating the need for surgically exposing, incising, removing, replacing, or bypassing the defective blood vessel.

Structures which have previously been used as intraluminal vascular grafts have included coiled stainless steel springs; helically wound coil springs manufactured from an expandable heat-sensitive material; and expanding stainless steel stents formed of stainless steel wire in a zig-zag pattern. In general, the foregoing structures have one major disadvantage in common. Insofar as these structures must be delivered to the desired location within a given body passageway in a collapsed state, in order to pass through the body passageway, there is no effective control over the final, expanded configuration of each structure. For example, the expansion of a particular coiled spring-type graft is predetermined by the spring constant and modulus of elasticity of the particular material utilized to manufacture the coiled spring structure. These same factors predetermined the amount of expansion of collapsed stents formed of stainless steel wire in a zig-zag pattern. In the case of intraluminal grafts, or prostheses, formed of a heat sensitive material which expands upon heating, the amount of expansion is likewise predetermined by the heat expansion characteristics of the particular alloy utilized in the manufacture of the intraluminal graft.

Thus, once the foregoing types of intraluminal grafts are expanded at the desired location within a body passageway, such as within an artery or vein, the expanded size of the graft cannot be changed. If the diameter of the desired body passageway has been miscalculated, an undersized graft might not expand enough to contact the interior surface of the body passageway, so as to be secured thereto. It may then migrate away from the desired location within the body passageway. Likewise, an oversized graft might expand to such an extent that the spring force, or expansion force, exerted by the graft upon the body passageway could cause rupturing of the body passageway. Further, the constant outwardly radiating force exerted upon the interior surface of the body passageway can cause erosion of the internal surface, or intima, of the artery or body passageway.

Another alternative to conventional vascular surgery has been percutaneous balloon dilation of elastic vascular stenoses, or blockages, through use of a catheter mounted angioplasty balloon. In this procedure, the angioplasty balloon is inflated within the stenosed vessel, or body passageway, in order to shear and disrupt the wall components of the vessel to obtain an enlarged lumen. With respect to arterial atheroscleerotic lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Although the balloon dilation procedure is typically conducted in the catherization lab of a hospital, because of the foregoing problem, it is always necessary to have a surgeon on call should the intimal flap block the blood vessel or body passageway. Further, because of the possibility of the intimal flap tearing away from the blood vessel and blocking the lumen, balloon dilations cannot be performed upon certain critical body passageways, such as the left main coronary artery, which leads into the heart. If an intimal flap formed by a balloon dilation procedure abruptly comes down and closes off a critical body passageway, such as the left main coronary artery, the patient could die before any surgical procedures could be performed.

Additional disadvantages associated with balloon dilation of elastic vascular stenoses is that many fail because of elastic recoil of the stenotic lesion. This usually occurs due to a high fibrocollagenous content in the lesion and is sometimes due to certain mechanical characteristics of the area to be dilated. Thus, although the body passageway may initially be successfully expanded by a balloon dilation procedure, subsequent, early restenosis can occur due to the recoil of the body passageway wall which decreases the size of the previously expanded lumen of the body passageway. For example, stenoses of the renal artery at the ostium are known to be refractory to balloon dilation because the dilating forces are applied to the aortic wall rather than to the renal artery itself. Vascular stenoses caused by neointimal fibrosis, such as those seen in dialysis-access fistulas, have proved to be difficult to dilate, requiring high dilating pressures and larger balloon diameters. Similar difficulties have been observed in angioplasties of graft-artery anastomotic strictures and postendarterectomy recurrent stenoses. Percutaneous angioplasty of Takayasu arteritis and neurofibromatosis arterial stenoses may show poor initial response and recurrence which is believed due to the fibrotic nature of these lesions.

Accordingly, prior to the development of the present invention, there has been no expandable intraluminal vascular graft, and method and apparatus for expanding the lumen of a body passageway, which: prevents recurrence of stenoses in the body passageway; can be utilized for critical body passageways, such as the left main coronary artery of a patient's heart; prevents recoil of the body passageway wall; and allows the intraluminal graft to be expanded to a variable size to prevent migration of the graft away from the desired location; and to prevent rupturing and/or erosion of the body passageway by the expanded graft. Therefore, the art has sought an expandable intraluminal vascular graft, and method and apparatus for expanding the lumen of a body passageway which: prevents recurrence of stenoses in the body passageway; is believed to be able to be utilized in critical body passageways, such as the left main coronary artery of the heart; prevents recoil of the body passageway; and can be expanded to a variable size within the body passageway to prevent migration of the graft away from the desired location; and to prevent rupturing and/or erosion of the body passageway by the expanded graft.

SUMMARY OF THE INVENTION

In accordance with the invention the foregoing advantages have been achieved through the present expandable intraluminal vascular graft. The present invention includes a thin-walled tubular member having first and second ends and a wall surface disposed between the first and second ends, the walls surface having a substantially uniform thickness and a plurality of slots formed therein, the slots being disposed substantially parallel to the longitudinal axis of the tubular member; the tubular shaped member having a first diameter which permits intraluminal delivery of the thin-walled tubular member into a body passageway having a lumen; and the tubular member having a second, expanded diameter, upon the application from the interior of the tubular member of a radially, outwardly extending force, which second diameter is variable and dependent upon the amount of force applied to the tubular member, whereby the tubular shaped member may be expanded and deformed to expand the lumen of the body passageway.

A further feature of the present invention is that the slots may be uniformly and circumferentially spaced from adjacent slots and the slots may be uniformly spaced from adjacent slots along the longitudinal axis of the tubular member, whereby at least one elongate member is formed between adjacent slots. Another feature of the present invention is that each slot may have first and second ends, and the first and second ends of each slot are disposed intermediate the first and second ends of adjacent slots along the longitudinal axis of the tubular member. An additional feature of the present invention is that the tubular member does not exert any outward, radial force while the tubular member has the first or second, expanded diameter. A further feature of the present invention is that the tubular shaped member may have a biological inert coating on its wall surface, and the coating may include a means for anchoring the tubular shaped member to the body passageway.

In accordance with the invention, the foregoing advantages have also been achieved through the present method for implanting a prosthesis within a body passageway. The method of the present invention comprises the steps of: utilizing a thin-walled, tubular member as the prosthesis, the tubular member having a plurality of slots formed therein, the slots being disposed substantially parallel to the longitudinal axis of the tubular member; disposing the prosthesis upon a catheter; inserting the prosthesis and catheter within the body passageway by catheterization of said body passageway; and expanding and deforming the prosthesis at a desired location within the body passageway by expanding a portion of the catheter associated with the prosthesis to force the prosthesis radially outwardly into contact with the body passageway, the prosthesis being deformed beyond its elastic limit.

A further feature of the present invention is that the portion of the catheter in contact with the prosthesis may be collapsed, and the catheter removed from the body passageway. A further feature of the present invention is that a catheter having an expandable, inflatable portion associated therewith may be utilized; and expansion of the prosthesis and the portion of the catheter is accomplished by inflating the expandable, inflatable portion of the catheter.

A further feature of the present invention is that the slots may be uniformly and circumferentially spaced from adjacent slots and the slots may be uniformly spaced from adjacent slots along the longitudinal axis of the tubular member, whereby at least one elongate member is formed between adjacent slots. Another feature of the present invention is that each slot may have first and second ends, and the first and second ends of each slot are disposed intermediate the first and second ends of adjacent slots along the longitudinal axis of the tubular member.

In accordance with the invention, the foregoing advantages have also been achieved through the present apparatus for intraluminally reinforcing a body passageway. The present invention includes: an expandable and deformable, thin-walled tubular prosthesis having first and second ends and a wall surface disposed between the first and second ends, the wall surface having a plurality of slots formed therein, the slots being disposed substantially parallel to the longitudinal axis of the prosthesis; and a catheter, having an expandable, inflatable portion associated therewith and including means for mounting and retaining the expandable and deformable tubular prosthesis on the expandable, inflatable portion, whereby upon inflation of the expandable, inflatable portion of the catheter, the prosthesis is expanded and deformed radially outwardly into contact with the body passageway. A further feature of the present invention is that the mounting and retaining means may comprise a retainer ring member disposed on the catheter adjacent the expandable, inflatable portion and adjacent each end of the expandable and deformable tubular prosthesis.

The expandable intraluminal vascular graft, method for implanting a prosthesis within a body passageway, and apparatus for intraluminally reinforcing a body passageway of the present invention, when compared with previously proposed prior art intraluminal grafts, methods for implanting them, and balloon dilation techniques have the advantages of: preventing recurrence of stenoses; is believed to permit implantation of grafts in critical body passageways, such as in the left main coronary artery of the heart; prevents recoil of the body passageway; prevents erosion of the body passageway by the expanded graft; and permits expansion of the graft to a variable size dependent upon conditions within the body passageway.

BRIEF DESCRIPTION OF THE DRAWINGS

In the drawings:

FIG. 1A is a perspective view of an expandable intraluminal vascular graft, or prosthesis for a body passageway, having a first diameter which permits delivery of the graft, or prosthesis, into a body passageway;

FIG. 1B is a perspective view of the graft, or prosthesis, of FIG. 1A, in its expanded configuration when disposed within a body passageway;

FIG. 2 is a cross-sectional view of the prosthesis taken along line 2-2 of FIG. 1B;

FIG. 3 is a cross-sectional view of an apparatus for intraluminally reinforcing a body passageway, or for expanding the lumen of a body passageway, illustrating a prosthesis, or intraluminal vascular graft, in the configuration shown in FIG. 1A;

FIG. 4 is a cross-sectional view of the apparatus for intraluminally reinforcing a body passageway, or for expanding the lumen of a body passageway, with the graft, or prosthesis, in the configurations shown in FIG. 1B; and FIGS. 5 and 6 are perspective views of prostheses for a body passageway, with the grafts, or prostheses, having a coating thereon.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION:

In FIGS. 1A and 1B, an expandable intraluminal vascular graft, or expandable prosthesis for a body passageway, 70 is illustrated. It should be understood that the terms "expandable intraluminal vascular graft" and "expandable prosthesis" are interchangeably used to some extent in describing the present invention, insofar as the methods, apparatus, and structures of the present invention may be utilized not only in connection with an expandable intraluminal vascular graft for expanding partially occluded segments of a blood vessel, or body passageway, but may also be utilized for many other purposes as an expandable prosthesis for many other types of body passageways. For example, expandable prostheses 70 may also be used for such purposes as: (1) supportive graft placement within blocked arteries opened by transluminal recanalization, but which are likely to collapse in the absence of an internal support; (2) similar use following catheter passage through mediastinal and other veins occluded by inoperable cancers; (3) reinforcement of cathether created intrahepatic communications between portal and hepatic veins in patients suffering from portal hypertension; (4) supportive graft placement of narrowing of the esophagus, the intestine, the ureters, the urethra; and (5) supportive graft reinforcement of reopened and previously obstructed bile ducts. Accordingly, use of the term "prosthesis" emcompasses the foregoing usages within various types of body passageways, and the use of the term "intraluminal vascular graft" encompasses use for expanding the lumen of a body passageway. Further, in this regard, the term "body passageway" emcompasses any duct within the human body, such as those previously described, as well as any vein, artery, or blood vessel within the human vascular system.

Still with reference to FIGS. 1A and 1B, the expandable intraluminal vascular graft, or prosthesis, 70 is shown to generally comprise a tubular member 71 having first and second ends 72, 73 and a wall surface 74 disposed between the first and second ends 72, 73. Tubular member 71 has a first diameter, d, which, to be hereinafter described in greater detail, permits intraluminal delivery of the tubular member 71 into a body passageway 80 having a lumen 81 (FIG. 3). With reference to FIG. 1B, upon the application from the interior of the tubular member 71 of a radially, outwardly extending force, to be hereinafter described in greater detail tubular member 71 has a second, expanded diameter, d', which second diameter d' is variable in size and dependent upon the amount of force applied to deform the tubular member 71.

Tubular member 71, may be any suitable material which is compatible with the human body and the bodily fluids (not shown) with which the vascular graft, or prosthesis, 70 may come into contact. Tubular member 71 must also be made of a material which has the requisite strength and elasticity characteristics to permit the tubular member 71 to be expanded and deformed from the configuration shown illustrated in FIG. 1A to the configuration shown in FIG. 1B and further to permit the tubular member 71 to retain its expanded and deformed configuration with the enlarged diameter d' shown in FIG. 1B and resist radial collapse. Suitable materials for the fabrication of tubular member 71 would include silver, tantalum, stainless steel, gold, titanium or any suitable plastic material having the requisite characteristics previously described.

Preferably, tubular member 71 is initially a thin-walled stainless steel tube having a uniform wall thickness, and a plurality of slots 82 are formed in the wall surface 74 of tubular member 71. As seen in FIG. 1A when tubular member 71 has the first diameter d, the slots 82 are disposed substantially parallel to the longitudinal axis of the tubular member 71. As seen in FIG. 1A, the slots 82 are preferably uniformly and circumferentially spaced from adjacent slots 82, as by connecting members 77, which connecting members 77 preferably have a length equal to the width of slots 82, as seen in FIG. 1A. Slots 82 are further uniformly spaced from adjacent slots 82 along the longitudinal axis of the tubular member 71, which spacing is preferably equal to the width of connecting members 77. Thus, the formation of slots 82 results in at least one elongate member 75 being formed between adjacent slots 82, elongate member 75 extending between the first and second ends, 72, 73 of tubular member 71, as seen in FIG. 1A.

Still with reference to FIG. 1A, each slot will have first and second ends with a connecting member 77 disposed at the first and second ends of slots 82. Preferably, the first and second ends of each slot 82 are disposed intermediate the first and second ends of adjacent slots 82 along the longitudinal axis of the tubular member 71. Thus, connecting members 77, which are disposed at the first and second ends of each slot 82, and between elongate members 75, will in turn be disposed intermediate the first and second ends of adjacent slots 82 along the longitudinal axis of the tubular member 71. Accordingly, slots 82 are preferably uniformly and circumferentially spaced from adjacent slots, and slots 82 adjacent to one another along the longitudinal axis of tubular member 71 are in a staggered relationship with one another. Alternating slots disposed about the circumference of tubular member 71 at both the first and second ends 72, 73 of tubular member 71 will only have a length equal to approximately one-half of the length of a complete slot 82, such half-slot 82 being bounded by members 78, 79, at both the first and second ends 72, 73 of tubular member 71. Although the graft, or prosthesis, 70 of FIGS. 1A and 1B is illustrated to have a length approximately equal to the length of two slots 82, it should be apparent that the length of the graft 70 could be made longer or shorter as desired. Use of the term "slot" encompasses an opening whose length is substantially greater than its width, such as an elongated oval opening.

The foregoing described construction of graft, or prothesis, 70 permits graft, or prothesis, 70 to be expanded uniformly, and outwardly, into the configuration shown in FIG. 1B, upon the application of a suitable force from the interior of tubular member 71, as will be hereinafter described in greater detail. The expansion of tubular member 71 into the configuration shown in FIG. 1B is further uniform along the length of tubular member 71, not only because of the uniform spacing between slots 82, as previously described, but also because the thickness of the wall surface 74, or the thickness of connecting members 77, elongate members 75, and members 78, 79, is the same uniform thickness. As illustrated in FIG. 2, the uniform thickness of elongate member 75 is shown, and the preferred cross-sectional configuration of elongate member 75, connecting member 77, and members 78, 79, is illustrated, which configuration is rectangular. It should of course be understood by those skilled in the art, that the cross-sectional configuration of the foregoing components of graft, or prothesis, 70 could also be square. As will be hereinafter described in greater detail, it is preferable that the outer surface 74 of graft, or prothesis, 70, which would be in contact with the body passageway 80 FIG. 4), should be relatively smooth.

With reference to FIG. 1B, it is seen that after the graft, or prothesis 70, has been expanded and deformed into the configuration of FIG. 1B, the slots 82 will assume a substantially hexagonal configuration when the tubular member 71 has the second, expanded diameter, d', as shown in FIG. 1B. Such a hexagonal configuration will result when the slots 82 initially have a substantially rectangular configuration when the tubular member 71 has the first diameter, d, illustrated in FIG. 1A. It should be noted that were the width of slots 82 to be substantially reduced, whereby the length of connecting member 77 would approximate a single point intersection, the expansion of such a tubular member 71 would result in slots 82 assuming a configuration which would be substantially a parallelogram (not shown).

It should be noted that not only is tubular member 71 expanded from the configuration shown in FIG. 1A to achieve the configuration shown in FIG. 1B, but tubular member 71 is further "deformed" to achieve that configuration. By use of the term "deformed" is meant that the material from which graft, or prothesis, 70 is manufactured is subjected to a force which is greater than the elastic limit of the material utilized to make tubular member 71. Accordingly, the force is sufficient to permanently bend elongate members 75 whereby segments of the elongate members 75 pivot about connecting members 77 and move in a circumferential direction as they pivot, whereby the diameter of the tubular member 71 increases from the first diameter, d, to the expanded diameter, d', of FIG. 1B. The force to be applied to expand tubular member 71, which is applied in the manner which will be hereinafter described in greater detail, must thus be sufficient to not only expand tubular member 71, but also to deform elongate member 75, in the manner previously described, whereby the portions of the elongate members 75 which pivot about the ends of connecting members 77 do not "spring back" and assume their configuration shown in FIG. 1A, but rather retain the configuration thereof in FIG. 1B. Once graft, or prosthesis, 70 has been expanded and deformed into the configuration shown in FIG. 1B, graft, or prothesis 70, will serve to prevent a body passageway from collapsing as will be hereinafter described in greater detail. It should be noted that when tubular member 71 has the first diameter, d, shown in FIG. 1A, or after tubular member 71 has been expanded and deformed into the second, expanded diameter, d', of FIG. 1B, tubular member 71 does not exert any outward, radial force, in that tubular member 71 is not a "spring-like" or "self-expanding member", which would tend to exert an outwardly radial force.

With reference now to FIGS. 3 and 4, the methods and apparatus of the present invention will be described in greater detail. Once again, it should be understood that the methods and apparatus of the present invention are useful not only for expanding the lumen of a body passageway, such as an artery, vein, or blood vessel of the human vascular system, but are also useful to perform the previously described procedures to intraluminally reinforce other body passageways or ducts, as previously described. Still with reference to FIGS. 3 and 4, an expandable intraluminal vascular graft, or prosthesis, 70, of the type described in connection with FIGS. 1A and 1B, is disposed or mounted upon a catheter 83. Catheter 83 has an expandable, inflatable portion 84 associated therewith. Catheter 83 includes means for mounting and retaining 85 the expandable intraluminal vascular graft, of prosthesis, 70 on the expandable, inflatable portion 84 of catheter 83. Preferably, the mounting and retaining means 85 comprises retainer ring members 86 disposed on the catheter 83 adjacent the expandable inflatable portion 84 of catheter 83; and a retainer ring member 86 is disposed adjacent each end 72, 73 of the expandable intraluminal vascular graft, or prosthesis, 70. Preferably, as seen in FIG. 3, retainer ring members are formed integral with catheter 83, and the retainer ring member 86 adjacent the leading tip 87 of catheter 83 slopes upwardly and away from catheter tip 87 in order to protect and retain graft or prosthesis, 70 as it is inserted into the lumen 81 of body passageway 80, as to be hereinafter described in greater detail. The remaining retainer ring member 86 as shown in FIG. 3, slopes downwardly away from tip 87 of catheter 83, to insure easy removal of catheter 83 from body passageway 80. After expandable intraluminal graft, or prosthesis, 70 has been disposed upon catheter 83, in the manner previously described, the graft, or prosthesis, 70 and catheter 83 are inserted within a body passageway 80 by catheterization of the body passageway 80 in a conventional manner.

In a conventional manner, the catheter 83 and graft, or prosthesis, 70 are delivered to the desired location within the body passageway 80, whereat it is desired to expand the lumen 81 of body passageway 80 via intraluminal graft 70, or where it is desired to implant prosthesis 70. Fluoroscopy, and/or other conventional techniques may be utilized to insure that the catheter 83 and graft, or prosthesis, 70 are delivered to the desired location within the body passageway. Prosthesis, or graft, 70 is then expanded and deformed by expanding the expandable, inflatable portion 84 of catheter 83, whereby the prosthesis, or graft, 70 is expanded and deformed radially, outwardly into contact with the body passageway 80, as shown in FIG. 4. In this regard, the expandable, inflatable portion of catheter 83 may be a conventional angioplasty balloon 88. After the desired expansion and deformation of prosthesis, or graft, 70 has been accomplished, angioplasty balloon 88 may be collapsed, or deflated, and the catheter 83 may be removed in a conventional manner from body passageway 80. If desired, as seen in FIG. 3, catheter 83, having graft or prosthesis, 70 disposed thereon, may be initially encased in a conventional Teflon TM sheath 89, which is pulled away from prosthesis, or graft, 70, prior to expansion of the prosthesis, or graft, 70.

Still with reference to FIGS. 3 and 4, it should be noted that tubular member 71 of prosthesis, or graft, 70 initially has the first predetermined, collapsed diameter, d, as described in connection with FIG. 1A, in order to permit the insertion of the tubular member, 71 into the body passageway 80 as previously described. When it is desired to implant prosthesis 70 within a body passageway 80 for the purposes previously described, the prosthesis 70 is expanded and deformed to the second diameter, d', and the second, expanded diameter, d', is variable and determined by the internal diameter of the body passageway 80, as shown in FIG. 4. Accordingly, the expanded and deformed prosthesis 70, upon deflation of angioplasty balloon 88 will not be able to migrate from the desired location within the body passageway 80, nor will the expansion of the prosthesis 70 be likely to cause a rupture of the body passageway 80. Furthermore, insofar as prosthesis, or graft, 70 is not a "spring-like" or "self-expanding member", the prosthesis is not consistently applying an outward, radial force against the interior surface of body passageway 80 in excess of that required to resist radial collapse of the body passageway 80. Thus, erosion of the interior surface, or intima, of the artery or body passageway is prevented.

When it is desired to use expandable intraluminal graft 70 to expand the lumen 81 of a body passageway 80 having an area of stenosis, the expansion of intraluminal vascular graft 70 by angioplasty balloon 88, allows controlled dilation of the stenotic area and, at the same time controlled expansion and deformation of the vascular graft 70, whereby vascular graft 70 prevents the body passageway 80 from collapsing and decreasing the size of the previously expanded lumen 81. Once again, the second, expanded diameter d' of intraluminal vascular graft 70, as shown in FIG. 4, is variable and determined by the desired expanded internal diameter of body passageway 80. Thus, the expandable intraluminal graft 70 will not migrate away from the desired location within the body passageway 80 upon deflation of angioplasty balloon 88, nor will the expansion of intraluminal graft 70 likely cause a rupture of body passageway 80, nor any erosion as previously described. Further, should an intimal flap, or fissure, be formed in body passageway 80 at the location of graft 70, graft 70 will insure that such an intimal flap will not be able to fold inwardly into body passageway 80, nor tear loose and flow through body passageway 80. In the situation of utilizing graft 70 in the manner previously described to expand the lumen of a portion of a critical body passageway, such as the left main coronary artery, it is believed that the intimal flap will be unable to occlude the left main coronary artery of the heart and cause the death of the patient.

Because it is only necessary to inflate angioplasty balloon 88 one time in order to expand and deform graft 70, it is believed that a greater amount of endothelium, or inner layer of the intima, or inner surface of the body passageway, will be preserved, insofar as the extent of endothelial denudation during transluminal angioplasty is proportional to the balloon inflation time. Further, in theory, the amount of preserved endothelium should be large because in the expanded configuration of graft 70, potentially 80% of the endothelium is exposed through the openings or expanded slots 82 of graft 70. It is further believed that intact patches of endothelium within expanded slots 82 of graft 70 may result in a rapid, multicentric endothelialization pattern as shown by experimental studies.

With reference now to FIGS. 5 and 6, prostheses, or grafts, 70 of the type previously described in connection with FIGS. 1A and 1B are shown, and the tubular members 71 of grafts, or prostheses, 70 have a biologically inert coating 90 placed upon wall surfaces 74 of tubular shaped members 71. Examples of a suitable biologically inert coating would be porous polyurethane, Teflon TM, or other conventional biologically inert plastic materials. The coating 90 should be thin and highly elastic so as not to interfere with the desired expansion and deformation of prosthesis, or graft, 70. Coating 90 may be further provided with a means for anchoring 91 (FIG. 6) the tubular member 71 to the body passageway 80. Anchoring means 91 may be comprised of a plurality of radially, outwardly extending projections 92 formed on the coating 90. As seen in FIG. 6, the radially outwardly extending projections 92 could comprise a plurality of ridges 93, or other types of radially, outwardly extending projections. Further, it may be desirable to have a plurality of openings 94 formed in coating 90, as shown in FIG. 5, whereby the fluid contained in body passageway 80 can be in direct contact with the dilated, or expanded, body passageway area.

It is to be understood that the invention is not limited to the exact details of construction, operation, exact materials or embodiment shown and described, as obviously modifications and equivalents will be apparent to one skilled in the art. For example, the means for expanding the prosthesis or graft could be a plurality of hydraulically actuated rigid members disposed on a catheter, or a plurality of angioplasty balloons could be utilized to expand the prosthesis or graft. Accordingly, the invention is therefore to be limited only by the scope of the appended claims.

I claim:

1. A method for implanting a prosthesis within a body passageway comprising the steps of:
   utilizing a thin-walled, tubular member as the prosthesis, the tubular member having a plurality of slots formed therein, the slots being disposed substantially parallel to the longitudinal axis of the tubular member;
   disposing the prosthesis upon a catheter;

inserting the prosthesis and catheter within the body passageway by catheterization of said body passageway; and expanding and deforming the prosthesis at a desired location within the body passageway by expanding a portion of the catheter associated with the prosthesis to force the prosthesis radially outwardly into contact with the body passageway, the prosthesis being deformed beyond its elastic limit.

2. The method of claim 1, further including the steps of: collapsing the portion of the catheter associated with the prosthesis, and removing the catheter from the body passageway.

3. The method of claim 1, including the steps of: utilizing a catheter having an expandable, inflatable portion associated therewith; and the expansion and deformation of the prosthesis and the portion of the catheter is accomplished by inflating the expandable, inflatable portion of the catheter.

4. The method of claim 1, wherein the slots are uniformly and circumferentially spaced from adjacent slots and the slots are uniformly spaced from adjacent slots along the longitudinal axis of the tubular member, whereby at least one elongate member is formed between adjacent slots.

5. The method of claim 4, wherein each slot has first and second ends, and the first and second ends of each slot are disposed intermediate the first and second ends of adjacent slots along the longitudinal axis of the tubular member.

6. The method of claim 5, wherein the thin-walled tubular member and the elongate members disposed between adjacent slots have a uniform wall thickness.

7. The method of claim 1, wherein the thin-walled tubular member is expanded and deformed to a second diameter within the body passageway; the second, expanded diameter being variable and determined by the internal diameter of the body passageway, whereby the expanded thin-walled tubular member will not migrate from the desired location within the body passageway and the expansion of the thin-walled tubular member does not cause a rupture of the body passageway.

8. The method of claim 7, wherein the thin-walled tubular member is uniformly, outwardly expanded and deformed along its length.

9. The method of claim 1, wherein the thin-walled tubular member is provided with a biologically inert coating on the outer surface of the thin-walled tubular member.

10. The method of claim 9, wherein the coating is provided with a means for anchoring the prosthesis to the body passageway.

11. The method of claim 10, wherein the means for anchoring is the coating being provided with a plurality of radially, outwardly extending projections for engagement with the body passageway.

12. The method of claim 9, wherein the coating is provided with a plurality of openings to allow communication between the body passageway and the interior of the thin-walled tubular member.

13. An expandable intraluminal vascular graft, comprising:

a thin-walled tubular member having first and second ends and a wall surface disposed between the first and second ends, the wall surface having a substantially uniform thickness and a plurality of slots formed therein, the slots being disposed substantially parallel to the longitudinal axis of the tubular member;

the tubular member having a first diameter which permits intraluminal delivery of the tubular member into a body passageway having a lumen; and the tubular member having a second, expanded and deformed diameter, upon the application from the interior of the tubular member of a radially, outwardly extending force, which second diameter is variable and dependent upon the amount of force applied to the tubular member, whereby the tubular member may be expanded and deformed to expand the lumen of the body passageway.

14. The expandable intraluminal vascular graft of claim 13, wherein the slots are uniformly and circumferentially spaced from adjacent slots and the slots are uniformly spaced from adjacent slots along the longitudinal axis of the tubular member, whereby at least one elongate member is formed between adjacent slots.

15. The expandable intraluminal vascular graft of claim 14, wherein each slot has first and second ends, and the first and second ends of each slot are disposed intermediate the first and second ends of adjacent slots along the longitudinal axis of the tubular member.

16. The expandable intraluminal vascular graft of claim 13, wherein the tubular member does not exert any outward, radial force while the tubular member has the first or second, expanded diameter.

17. The expandable intraluminal vascular graft of claim 13, wherein the slots have a substantially rectangular configuration when the tubular member has the first diameter; and the slots have a substantially hexagonal configuration when the tubular member has the second, expanded diameter.

18. The expandable intraluminal vascular graft of claim 13, wherein the slots have a configuration which is substantially a parallelogram after the tubular member has been expanded and deformed into the second expanded diameter.

19. The expandable intraluminal vascular graft of claim 13, wherein the tubular member has a biologically inert coating on the wall surface.

20. The expandable intraluminal vascular graft of claim 19, wherein the coating includes a means for anchoring the tubular member to the body passageway.

21. The expandable intraluminal vascular graft of claim 20, wherein the anchoring means is a plurality of radially, outwardly extending projections formed on the coating.

22. The expandable intraluminal vascular graft of claim 19, wherein the coating has a plurality of openings therein to allow communication between the body passageway and the interior of the tubular member.

23. The expandable intraluminal vascular graft of claim 13, wherein the outside of the wall surface of the tubular member is a smooth surface, when the tubular member has the first diameter.

24. An expandable prosthesis for a body passageway, comprising:

a thin-walled tubular member having first and second ends and a wall surface disposed between the first and second ends, the wall surface having a substantially uniform thickness and a plurality of slots formed therein, the slots being disposed substantially parallel to the longitudinal axis of the tubular member;

the tubular member having a first diameter which permits intraluminal delivery of the tubular member into a body passageway having a lumen; and the tubular member having a second, expanded and deformed diameter, upon the application from the interior of the tubular member of radially, outwardly extending force, which second diameter is variable and dependent upon the amount of force applied to the tubular member, whereby the tubular member may be expanded and deformed to expand the lumen of the body passageway.

25. The expandable prosthesis for a body passageway of claim 24, wherein the tubular member has a biologically inert coating on the wall surface.

26. The expandable prosthesis for a body passageway of claim 25, wherein the coating includes a means for anchoring the tubular member to the body passageway.

27. The expandable prosthesis for a body passageway of claim 26, wherein the anchoring means is a plurality of radially, outwardly extending projections formed on the coating.

28. The expandable prosthesis for a body passageway of claim 25, wherein the coating has a plurality of openings therein to allow communication between the body passageway and the interior of the tubular member.

29. The expandable prosthesis of claim 24, wherein the the slots are uniformly and circumferentially spaced from adjacent slots and the slots are uniformly spaced from adjacent slots along the longitudinal axis of the tubular member, whereby at least one elongate member is formed between adjacent slots.

30. The expandable prosthesis of claim 29, wherein each slot has first and second ends, and the first and second ends of each slot are disposed intermediate the first and second ends of adjacent slots along the longitudinal axis of the tubular member.

31. The expandable prosthesis of claim 24, wherein the tubular member does not exert any outward, radial force while the tubular member has the first or second, expanded diameter.

32. The expandable prosthesis of claim 24, wherein the slots have a substantially rectangular configuration when the tubular member has the first diameter; and the slots have a substantially hexagonal configuration when the tubular member has the second, expanded diameter.

33. The expandable prosthesis of claim 24, wherein the slots have a configuration which is substantially a parallelogram after the tubular member has been expanded and deformed into the second expanded diameter.

34. The expandable prosthesis of claim 24, wherein the outside of the wall surface, of the tubular member is a smooth surface, when the tubular member has the first diameter.

35. An apparatus for intraluminally reinforcing a body passageway, comprising:

an expandable and deformable, thin-walled tubular prosthesis having first and second ends, and a wall surface disposed between the first and second ends, the wall surface having a plurality of slots formed therein, the slots being disposed substantially parallel to the longitudinal axis of the prosthesis; and a catheter, having an expandable, inflatable portion associated therewith and including means for mounting and retaining the expandable, thin-walled tubular prosthesis on the expandable, inflatable portion, whereby upon inflation of the expandable, inflatable portion of the catheter, the prosthesis is expanded and deformed radially outwardly into contact with the body passageway.

36. The apparatus of claim 35, wherein the mounting and retaining means comprises retainer ring members disposed on the catheter adjacent the expandable, inflatable portion and adjacent each end of the expandable, tubular prosthesis.

37. An apparatus for expanding the lumen of a body passageway comprising:

an expandable and deformable thin-walled intraluminal vascular graft having first and second ends, and a wall surface disposed between the first and second ends, the wall surface having a plurality of slots formed therein, the slots being disposed substantially parallel to the longitudinal axis of the graft; and a catheter, having an expandable, inflatable portion associated therewith and including means for mounting and retaining the expandable, deformable intraluminal vascular graft on the expandable, inflatable portion, whereby upon inflation of the expandable, inflatable portion of the catheter, the intraluminal vascular graft is expanded and deformed radially outwardly into contact with the body passageway.

38. The apparatus of claim 37, wherein the mounting and retaining means comprises retainer ring members disposed on the catheter adjacent the expandable, inflatable portion and adjacent each end of the expandable intraluminal vascular graft.

39. The method of claim 1, wherein tantalum is utilized for the tubular member.

40. The expandable intraluminal vascular graft of claim 13, wherein tantalum is utilized for the tubular member.

41. The expandable prosthesis of claim 24, wherein tantalum is utilized for the tubular member.

42. The apparatus of claim 35, wherein tantalum is utilized for the tubular prosthesis.

43. The apparatus of claim 37, wherein tantalum is utilized for the intraluminal vascular graft.

* * * * *

REEXAMINATION CERTIFICATE (3650th)
United States Patent [19]
Palmaz

[11] B1 4,739,762
[45] Certificate Issued Oct. 27, 1998

[54] EXPANDABLE INTRALUMINAL GRAFT, AND METHOD AND APPARATUS FOR IMPLANTING AN EXPANDABLE INTRALUMINAL GRAFT

[75] Inventor: Julio C. Palmaz, San Antonio, Tex.

[73] Assignee: Expandable Grafts Partnership, San Antonio, Tex.

Reexamination Request:
No. 90/004,785, Oct. 6, 1997

Reexamination Certificate for:
Patent No.: 4,739,762
Issued: Apr. 26, 1988
Appl. No.: 923,798
Filed: Nov. 3, 1986

Related U.S. Application Data

[63] Continuation-in-part of Ser. No. 796,009, Nov. 7, 1985, Pat. No. 4,733,665.

[51] Int. Cl.$^6$ .................................................. A61M 29/00
[52] U.S. Cl. ..................... 606/108; 604/104; 604/96; 623/1
[58] Field of Search ........................... 606/155, 156, 606/108, 198, 191, 195; 623/1, 12

[56] References Cited

U.S. PATENT DOCUMENTS

| | | | |
|---|---|---|---|
| Re. 34,327 | 7/1993 | Kreamer | 623/1 |
| 2,070,073 | 2/1937 | Walton | 210/499 |
| 2,854,982 | 10/1958 | Pagano | 128/348 |
| 2,854,983 | 10/1958 | Baskin | 604/96 |
| 3,334,629 | 8/1967 | Cohn | 128/325 |
| 3,526,005 | 9/1970 | Bokros et al. | 623/1 X |
| 3,540,431 | 11/1970 | Mobin-Udin | 128/1 R |
| 3,562,820 | 2/1971 | Braun | 3/1 |
| 3,599,641 | 8/1971 | Sheridan | 604/283 |
| 3,657,744 | 4/1972 | Ersek | 3/1 |
| 3,834,394 | 9/1974 | Hunter et al. | 128/325 |
| 3,858,441 | 1/1975 | Comeau | 138/93 |
| 3,874,388 | 4/1975 | King et al. | 128/334 |
| 3,893,344 | 7/1975 | Hunter | 128/325 |
| 3,952,747 | 4/1976 | Kimmell, Jr. | 128/1 R |
| 3,968,800 | 7/1976 | Vilasi | 128/343 |
| 4,047,252 | 9/1977 | Liebig et al. | 3/1.4 |
| 4,056,854 | 11/1977 | Boretos et al. | 3/1.5 |

(List continued on next page.)

FOREIGN PATENT DOCUMENTS

| | | | |
|---|---|---|---|
| 183 372 | 10/1985 | European Pat. Off. | |
| 0 177 330 A2 | 10/1986 | European Pat. Off. | |
| 0 274 846 A1 | 12/1987 | European Pat. Off. | 29/2 |
| 0 282 175 A1 | 2/1988 | European Pat. Off. | 29/2 |
| 2 410 933 | 3/1974 | Germany | |
| 3205942 A1 | 9/1983 | Germany | |
| 57-35985 | of 1982 | Japan | |
| 660689 | 5/1979 | U.S.S.R. | |
| 0669689 | 5/1979 | U.S.S.R. | |
| 0764684 | 9/1980 | U.S.S.R. | |
| 1 205 743 | 9/1970 | United Kingdom | |
| WO 83/03752 | 4/1983 | WIPO | |

OTHER PUBLICATIONS

The rationale For Patch–Graft Angioplasty After Carotid Endarterectomy: Early and Long–Term Follow–Up. Stroke, vol. 15, No. 6, Nov. 1984.

Aterial Vascular Engineering, Inc.'s First Amended Complaint For Declaratory Relief Of patent Invalidity, Unenforceability, Noninfringement, And For Antitrust Violations (Jan. 27, 1998), *Arterial Vascular Engineering, Inc. v. Cordis Corporation, Johnson & Johnson and Expandable Grafts Partnership,* Civil Action No. 97–700.

(List continued on next page.)

*Primary Examiner*—Michael H. Thaler

[57] ABSTRACT

An expandable and deformable intraluminal vascular graft is expanded within a blood vessel by an angioplasty balloon associated with a catheter to dilate and expand the lumen of a blood vessel. The graft may be a thin-walled tubular member having a plurality of slots disposed substantially parallel to the longitudinal axis of the tubular member.

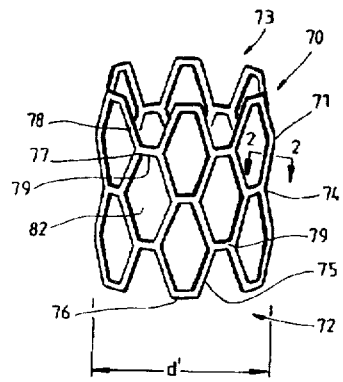 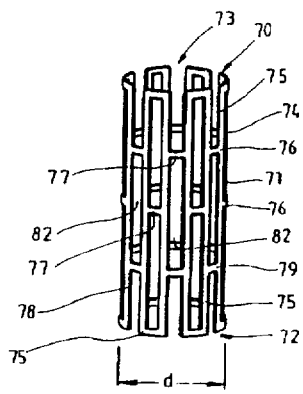

U.S. PATENT DOCUMENTS

| | | | |
|---|---|---|---|
| 4,061,134 | 12/1977 | Samuels et al. | 128/1 |
| 4,076,285 | 2/1978 | Martinez | 285/332 |
| 4,105,022 | 8/1978 | Anthoshkiw et al. | 128/2.05 F |
| 4,140,126 | 2/1979 | Choudhury | 128/334 |
| 4,190,909 | 3/1980 | Ablaza | 3/1.4 |
| 4,195,637 | 4/1980 | Gruntzig et al. | 128/348 |
| 4,198,982 | 4/1980 | Fortner et al. | 128/334 |
| 4,214,587 | 7/1980 | Sakura, Jr. | 128/334 |
| 4,295,464 | 10/1981 | Shihata | 128/1 |
| 4,299,226 | 11/1981 | Banka | 128/344 |
| 4,300,244 | 11/1981 | Bokros | 3/1.4 |
| 4,313,231 | 2/1982 | Koyamada | 3/1.4 |
| 4,319,363 | 3/1982 | Ketharanathan | 3/1.4 |
| 4,340,046 | 7/1982 | Cox | 128/207.17 |
| 4,390,599 | 6/1983 | Broyles | 428/597 |
| 4,448,195 | 5/1984 | Le Veen et al. | 128/344 |
| 4,479,497 | 10/1984 | Fogarty | 128/344 |
| 4,493,711 | 1/1985 | Chin et al. | 604/271 |
| 4,494,531 | 1/1985 | Gianturco | 128/1 R |
| 4,503,569 | 3/1985 | Dotter | 128/303 R |
| 4,512,338 | 4/1985 | Balko et al. | 128/341 |
| 4,531,933 | 7/1985 | Norton et al. | 604/8 |
| 4,550,447 | 11/1985 | Seiler, Jr. et al. | 623/1 |
| 4,560,374 | 12/1985 | Hammerslag | 604/49 |
| 4,572,186 | 2/1986 | Gould et al. | 128/341 |
| 4,577,631 | 3/1986 | Kreamer et al. | 623/12 X |
| 4,586,505 | 5/1986 | Sisson et al. | 128/344 |
| 4,604,762 | 8/1986 | Robinson | 623/1 |
| 4,617,932 | 10/1986 | Kornberg | 623/1 X |
| 4,619,261 | 10/1986 | Guerriero | 128/325 |
| 4,641,653 | 2/1987 | Rockey | 604/96 |
| 4,643,184 | 2/1987 | Mobin-Udin | 128/345 |
| 4,647,416 | 3/1987 | Seiler, Jr. et al. | 264/118 |
| 4,649,922 | 3/1987 | Wiktor | 128/344 |
| 4,655,771 | 4/1987 | Wallsten | 623/1 |
| 4,660,560 | 4/1987 | Klein | 128/344 |
| 4,665,918 | 5/1987 | Garza et al. | 128/343 |
| 4,676,241 | 6/1987 | Webb et al. | 128/207 |
| 4,681,110 | 7/1987 | Wiktor | 128/343 |
| 4,699,611 | 10/1987 | Bowden | 604/1 |
| 4,705,517 | 11/1987 | DiPisa, Jr. | 623/12 |
| 4,710,181 | 12/1987 | Fuqua | 604/280 |
| 4,723,549 | 2/1988 | Wholey et al. | 128/344 |
| 4,731,054 | 3/1988 | Billeter et al. | 604/93 |
| 4,733,665 | 3/1988 | Palmaz | 128/343 |
| 4,740,207 | 4/1988 | Kreamer | 623/1 |
| 4,760,849 | 8/1988 | Kropf | 128/341 |
| 4,768,507 | 9/1988 | Fischell et al. | 128/303 |
| 4,771,773 | 9/1988 | Kropf | 128/303 |
| 4,776,337 | 10/1988 | Palmaz | 128/343 |
| 4,787,899 | 11/1988 | Lazarus | 623/1 |
| 4,842,575 | 6/1989 | Hoffman, Jr. et al. | 600/36 |
| 4,848,343 | 7/1989 | Wallsten et al. | 128/343 |
| 4,875,480 | 10/1989 | Imbert | 128/343 |
| 4,877,030 | 10/1989 | Beck et al. | 623/1 X |
| 4,878,906 | 11/1989 | Lindemann et al. | 623/1 |
| 4,902,289 | 2/1990 | Yannas | 623/1 |
| 4,954,126 | 9/1990 | Wallsten | 600/36 |
| 4,994,032 | 2/1991 | Sugiyama et al. | 604/96 |
| 4,998,539 | 3/1991 | Delsanti | 128/898 |
| 4,998,923 | 3/1991 | Samson et al. | 606/194 |
| 5,037,392 | 8/1991 | Hillstead | 604/96 |
| 5,041,126 | 8/1991 | Gianturco | 606/195 |
| 5,059,211 | 10/1991 | Stack et al. | 606/198 |
| 5,061,275 | 10/1991 | Wallsten et al. | 623/1 |
| 5,102,417 | 4/1992 | Palmaz | 606/195 |
| 5,104,399 | 4/1992 | Lazarus | 623/1 |
| 5,192,307 | 3/1993 | Wall | 623/1 |
| 5,266,073 | 11/1993 | Wall | 623/1 |
| 5,275,622 | 1/1994 | Lazarus et al. | 623/1 |
| 5,306,286 | 4/1994 | Stack et al. | 606/198 |
| 5,314,444 | 5/1994 | Gianturco | 606/195 |
| 5,397,345 | 3/1995 | Lazarus | 623/1 |
| 5,527,336 | 6/1996 | Rosenbluth et al. | 606/192 |
| 5,562,728 | 10/1996 | Lazarus et al. | 623/1 |
| 5,662,700 | 9/1997 | Lazarus | 623/1 |
| 5,669,936 | 9/1997 | Lazarus | 623/1 |
| B1 4,733,665 | 1/1994 | Palmaz | 606/108 |

OTHER PUBLICATIONS

Cordis Corporation and Expandable Grafts Partnership's Complaint And Demand For Jury Trial (Feb. 6, 1998), *Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.,* Delaware District Court Case No. 98–65.

Cordis Corporation's Motion to Amend the Complaint and to Add a Party (Feb. 2, 1998), *Cordis Corporation v. Advanced Cardiovascular Systems, Inc., Guidant Corporation, Arterial Vascular Engineering, Inc., Boston Scientific Corporation and SCIMED Life Systems, Inc.,* Delaware District Court Case No. 97–550–SLR.

Cordis Corporation's Motion For Consolidation Pursuant to Rule 42(a) (Feb. 6, 1998), *Cordis Corporation v. Advanced Cardiovascular Systems, Inc., Guidant Corporation, Arterial Vascular Engineering, Inc., Boston Scientific Corporation and SCIMED Life Systems, Inc.,* Delaware District Court Case No. 97–550–SLR and *Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.,* Delaware District Court Case No. 98–65.

Cordis Corporation's Answer and Counterclaim (Feb. 27, 1998), *Arterial Vascular Engineering, Inc. v. Cordis Corporation et al.,* Delaware District Court Case No. 97–700–SLR.

Expandable Grafts Partnership's Answer To Arterial Vascular Engineering, Inc.'s First Amended Complaint; And Counterclaim Jul. 27, 1998), *Arterial Vascular Engineering, Inc. v. Cordis Corporation et al.,* Delaware District Court Case No. 97–700–SLR.

Reply of Plaintiff Arterial Vascular Engineering, Inc. To Counterclaims of Defandant Cordis Corporation (Mar. 31, 1998), *Arterial Vasciular Engineering, Inc. v. Cordis Corporation et al.,* Delaware District Court Case No. 97–700–SLR.

Reply of Plaintiff Arterial Vascular Engineering, Inc. To Counterclaims of Defendant Expandable Grafts Partnership (Mar. 31, 1998), *Arterial Vascular Engineering, Inc. v. Cordis Corporation et al.,* Delaware District Court Case No. 97–700–SLR.

Answer and Counterclaims of Defendant Advanced Cardiovascular Systems, Inc. (Mar. 9, 1998), *Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.,* Delaware District Court Civil Action No. 97–550–SLR (Consolidated).

Boston Scientific Corporation and SCIMED Life Systems, Inc.'s Answer to the Second Amended Complaint in Case No. 97–550 and to the Identical Compliant Assigned Case No. 98–65 (Apr. 15, 1998), *Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.,* Delaware District Court Civil Action No. 97–550–SLR.

Expandable Grafts Partnership's EGP's Answers and Objections to AVE's First Set of Interrogatories (Mar. 22, 1998), *Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.,* Delaware District Court Civil Action No. 97–550–SLR.

Defendant Arterial Vascular Engineering, Inc.'s Responses to Plantiff's First Set of Interrogatories Nos. 1–13 (Apr. 28, 1998), *Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.,* Delaware District Court Civil Action No. 97–550–SLR.

Advanced Cardiovascular Systems, Inc. and Guidant Corporation's First Supplemental Response to Plaintiff's First Set of Interrogatories (No. 11) (Feb. 3, 1998), *Corida Corporation v. Advanced Cardiovascular Systems, Inc., Guidant Corporation, Arterial Vascular Engineering, Inc., Boston Scientific Corporation and SCIMED Life Systems, Inc.,* Delaware District Court Civil Action No. 97–550–SLR.

Boston's Skleton Argument (undated), *Boston Scientific Limited and Boston Scientific International B.V. v. Expandable Grafts Partnership and Boston Scientific Limited and Boston Scientific International B.V. v. Julio C. Palmaz* High Court of Justice, Chancery Division, Patents Court.

Skelton Argument of Palmaz/EGP (undated), *Boston Scientific Limited and Boston Scientific International B.V. v. Julio C. Palmaz and Expandable Grafts Partnership,* High Court of Justice, Chancery Division, Patents Court.

Boston's Closing Submissions (undated), *Boston Scientific Limited and Boston Scientific International B.V. v. Expandable Grafts Partnership and Boston Scientific Limited and Boston Scientific International B.V. v. Julio C. Palmaz* High Court of Justice, Chancery Division, Patents Court.

EGP's Final Submissions (undated), *Boston Scientific Limited and Boston Scientific International B.V. v. Julio C. Palmaz and Expandable Grafts Partnership,* High Court of Justice, Chancery Division, Patents Court.

Judgment (Jun. 26, 1998), *Boston Scientific Limited and Boston Scientific International B.V. v. Julio C. Palmaz and Expandable Grafts Partnership,* High Court of Justice, Chancery Division, Patents Court.

Affidavit of Dr. Julio C. Palmaz (Dec. 5, 1997), *Boston Scientific Limited and Boston Scientific International B.V. v. Julio C. Palmaz,* High Court of Justice, Chancery Division, Patents Court.

Affidavit of Ben D. Tobor (Dec. 8, 1997), *Boston Scientific Limited and Boston Scientific International B.V. v. Julio C. Palmaz,* High Court of Justice, Chancery Division, Patents Court.

Affidavit of Martin Aufenanger (Dec. 8, 1997), *Boston Scientific Limited and Boston Scientific International B.V. v. Julio C. Palmaz,* High Court of Justice, Chancery Division, Patents Court.

Deposition of Nigel P. Buller, M.D. (Dec. 20, 1997), *Cordis Corporation v. Advanced Cardiovascular Systems,* District Court of Delaware Case No. 97–550.

Deposition of Alfred Steward Windeler, Ph.D. (Jan. 28, 1998), *Cordis Corporation v. Advanced Cardiovascular Systems,* District Court of Delaware Case No. 97–550.

Deposition of Richard A. Bowman (Jan. 9, 1998), *Cordis Corporation v. Advanced Cardiovascular Systems,* District Court of Delaware Case No. 97–550.

Deposition of Gary Schneiderman (Jan. 16, 1998), *Cordis Corporation v. Advanced Cardiovascular Systems,* District Court of Delaware Case No. 97–550.

Deposition of Julio Cesar Palmaz (Dec. 29, 1997), *Cordis Corporation v. Advanced Cardiovascular Systems,* District Court of Delaware Case No. 97–550.

"Repositioning of Biliary Endoprosthesis with Gruntzig Balloon Catheters," EP Harries–Jones, S Fataar and EJ Tuft, *AJR* 138:771–772 (Apr. 1982).

"Effect of Maxillary Osteotomy on Subsequent Craniofacial Growth in Adolescent Monkeys," R Nanda, J. Sugawara and RG Topazian, *Am J Orthod* (May 1983).

"Expandable Intraluminal Vascular Graft: A Feasibility Stidy," J. Palmaz, R. Sibbitt, F. Tio, S. Reuter, J. Peters, F. Garcia, *Surgery,* vol. 99, pp. 199–205 (Feb. 1986).

"Atherosclerotic Rabbit Aortas: Expandable Intraluminal Grafting", J. Palmaz, S. Windeler, F. Garcia, F. Tio, R. Sibbitt, S. Reuter, *Radiology,* vol. 160, pp. 723–726 (Sep. 1986).

*JACC,* vol. 9, No. 2, Abstracts p. 106A (Feb. 1987).

"Intravascular Stents to Prevent Occlusion and Restenosis After Transluminal Angioplasty," U Sigward, J Puel, V Mirkovitch, F Joffre and L Kappenberger, *N Engl J Med,* 316:701–6 (Mar. 19, 1987).

"Percutaneous Endovascular Graft: Experimental Evaluation," DD Lawrence, C Charnsangavej, KC Wright, C Gianturco and S Wallace, *Radiology,* 163:357–360 (May 1987).

"Self–Expanding Metallic Stents: Preliminary Evaluation in an Atherosclerotic Model," N Rollins, KC Wright, C Cjarnsangavej, S Wallace and C Gianturco, *Radiology,* vol. 163, No. 3, pp. 739–742 (Jun. 1987).

"Balloon–Expandable Intracoronary Stents in the Adult Dog," RA Schatz, JC Palmaz, FO Tio, F Garcia, O Garcia and SR Reuter, *Circulation,* vol. 76, No. 2, pp. 450–457 (Aug. 1987).

"Self–Expanding Endovascular Prosthesis: An Experimental Study," H Rosseau, J Puel, F Joffre, U Sigwart, C Duboucher, C Imbert, C Knight, L Kropf and H Wallsten, *Radiology,* 164:709–714 (Sep. 1987).

"Normal and Stenotic Renal Arteries: Experimental Balloon–Expandable Intraluminal Stenting," JC Palmaz, DT Kopp, H Hayashi, RA Schatz, G Hunter, FO Tio, O Garcia, R Alvarado, C Rees and SC Thomas, *Radiology,* 164:705–708 (Sep. 1987).

"Gianturco Expandable Wire Stents in the Treatment of Superior Vena Cava Syndrome Recurring After Maximum–Tolerance Radiation," J Rosch, JE Bedell, J Putnam, R Antonovic and B Uchida, *Cancer,* 60:1243–1236 (Sep. 15, 1987).

"One Year of Percutaneous Coronary Stenting,", U Sigwart, C Imbert, A Essinger, A Fischer, H Sadeghi L Kappenberger, *Circulation,* P II, vol. 76, No. 4 (Oct. 1987).

"Early and Late Results of Inracoronary Arterial Stenting After Coronary Angioplasty in Dogs" GS Roubin, KA Robinson, SB King, C Gianturco, AJ Black, JE Brown, RJ Siegel and JS Douglas, *Circulation*, vol. 76, No. 4, pp. 891–897 (Oct. 1987).

"Intravascular Stents to Prevent Restenosis After Transluminal Coronary Angioplasty," J Puel, H Rosseau, F Joffre, S Hatem, JM Fauvel, JP Bounhoure and CT Rangueil, *Circulation*, Pt. II, vol. 76, No. 4, 0105 (Oct. 1987).

"Abstracts From the 60th Scientific Sessions," *Circulation*, Pt. II, vol. 76, No. 4, IV–232 (Oct. 1987).

"Balloon Expandable Intra–Arterial Stents: Effect of Anticoagulation on Thrombus Formation," *Circulation*, JC Palmaz, OJ Garcia, DT Kopp, RA Schatz, FO Tio, and V Claravino, *Circulation*, Pt. II, vol. 76, No. 4 (Oct. 1987). *J Cardiovasc. Surg.*, vol. 28, No. 5, pp. 39–41 (Sep.–Oct. 1987).

"Perkutan Implantierbare, Durch Ballon Aufdehnbare Gefäßprothese," EP Strecker, P Romaniuk, B Schneider, M Westphal, E Zeitler, HRD Wolfund and N Freudenberg, *Disch Med Wschr*, 113:538–542 (1988).

"Modified Gianturco Expandable Wire Stents in Experimental and Clinical Use," J Rosch, JSE Putnam and BT Uchida, *Cirse, Porto Cervo*, vol. 31, No. 2, pp. 100–103 (1988).

"Implantation of Balloon–Expandable Intravascular Grafts by Catherization in Pulmonary Arteries and Systemic Veins," CE Mullins, MP O'Laughlin, GW Vick, DC Mayem RJ Myers, DL Kearney, RA Schatz and JC Palmaz, *Circulation*, vol. 77, No. 1, pp. 188–199 (1988).

"Modifications of Gianturco Expandable Wire Stents," BT Uchida, JS Putnam and J Rösch, *AJR*, 150:1185–1187 (May 1988).

Dotter, Charles T. and Judkins, Melvin P., "Transluminal Treatment of Arteriosclerosis Obstruction," Circulation 1964; 30:654–670 (CO31558–575).

Rashkind W.J/, Miller, W.W.: Creation of an atrial septal defect without thoracotomy: A palliative approach to complete transposition of the great arteries. *JAMA*, 1966, 196; 991–92.

Peter Eichelter, MD, and Worthington G. Schenk, Jr.,MD Buffalo, "Prophylaxis of Pulmonary Embolism", *Arch Surg*–vol. 97, Aug. 1968, pp. 348–356.

James W. Pate, M.C., F.A.C.S., David Melvin, M.D., Richard C. Cheek, M.D., "A New Form of Vena Caval Interruption", *Annals of Surgery*, Jun. 1969, pp. 873–880.

Kazi Mobin–Uddin, MB, BS; Robert McLean; Hooshang Bolooki, MD; and James R. Jude, MD, Coral Gables, Fla., "Caval Interruption for Prevention of Pulmonary Embolism", *Arch Surg*/vol. 99, Dec. 1969.

James A. Hunter, M.D., Robert Sessions, Richard Buenger, M.D., "Experimental Balloon Obstruction of the Inferior Vena Cava", *Annals of Surgery*, Feb. 1970, pp. 315–320.

Lazar Greenfield, M.D., James R. McCurdy, M.D., Phillip P. Brown, M.D., and Ronald C. Elkins, M.D., Oklahoma City, Okla.,: "A New Intracaval Filter Permitting Continued Flow and Resolution of Emboli", Apr. 1973, *Surgery*, vol. 73, No. 4, pp. 599–606.

Kazi Modin–Uddin, Joe R. Utley, and Lester R. Bryant, "The Inferior Vena Cava Umbrella Filter", *Progress in Cardiovascular Diseases*, vol. XVII, No. 5, (Mar./Apr.), 1975, pp. 391–399.

Goldstein et al., "Transcather Occlusion of Abdominal Tumors" *Radiology* 120: 539–545 (Sep. 1976) (C14058–65).

Morris Simon, M.D., Roy Kaplow, Ph.D., Edwin Salzman, M.D., and David Freiman, M.D., "A Vena Cava Filter Using Thermal Shape Memory Alloy", *Radiology*, 125: pp. 89–94, Oct. 1977.

The Surgical Experience and a One to Sixteen Year Follow–Up of 277 Abdominal Aortic Aneurysm. Gardner et al., American Journal of Surgery, 135, pp. 226–230 (1978).

Edwards, "Arterial Grafts" *Archives of Surgery*, 113: 1225–33 (Nov. 1978) (C14200–208).

Lunderquist et al., "Guidewire for Percutaneous Transheptic Cholangiography," *Radiology* 132: 228 (Jul. 1979) (C14114–15).

Campbell et al., "Expanded Microporous Polytetra Fluoroethylene as a Vascular Substitute: A two year Follow Up," *Surgery* 85: 177–78 (1979) (C14193–199).

Semb B.K.H., Tjonneland, S., Stake G., et al.: "Balloon valvotomy" of congenital pulmonary valve steonsis with tricuspid valve insufficiency. *Cardiovasc. Radial.*, 1979; 2:238–241.

Hoevels et al., "Percutaneous Transheptic Insertion of a Permanent Endoprosthesis in Obstructive Lesions of the Extrahepatic Bile Ducts," *Gastrointest. Radiol.* 4: 367–77 (1979) (C14402–13).

George E. Cimochowsky, M.D., Richard H. Evans, M.D., Christopher K. Zairins, M.D., Chien–Tai Lu, M.D., and Tom R. DeMeester, M.D., Chicago, Ill., "Greenfield Filter Versus Mobin–Uddin Umbrella", *J Thorac Cardiovac Surg*, 79: pp. 358–363, 1980.

Cope, "Balloon Dilatation of Closed Mesocaval Shunts," *AJR* 135: 989–993 (Nov. 1980) (C14337–41).

Dotter, Charles T., "International Radiology–Review of an Emerging Field," Seminars in Roentgenology, vol. XVI, No. 1 |Jan.| 1981 (C029209–210).

Smith et al., "Safe and Effective Catheter Angiography Through Prosthetic Vascular Grafts," *Radiology* 138: 487–88 (Feb. 1981) (C14216–17).

Fogarty, T.J.; Chin, A., Shoor, P.M., et al.: Adjunctive intraoperative arterial dilation: Simplified instrumentation technique. *Arch. Surg.* 1981, 116(11): 1391–8.

Harries–Jones et al., "Repositioning of Biliary Endoprothesis with Grüntzig Balloon Catheters," *AJR* 138: 771–772 (Apr. 1982) (C13820–22).

Honickman et al., "Malpositioned Biliary Endoprosthesis: Retrieval Using a Vascular Balloon Catheter," *Radiology* 144: 423–425 (Jul. 1982) (C13817–19).

Ring et al. "A Simple, Indwelling Biliary Endoprosthesis Made from Commonly Available Catheter Material" *AJR* 139: 615–617 (Sep. 1982) (C14054–57).

Aubrey M. Palestrant, M.D., Martin Prince, B.S., Morris Simon, M.D., "Comparative In Vitro Evaluation of the Nitinol Inferior Vena Cava Filter", *Radiology*: 145, pp. 351–355, Nov. 1982.

Kan, J.S., White R.I., Mitchell, S.E.: et al.: Percutaneous balloon valvuloplasty: A new method for treating congenital valve stenosis. *N. Eng J Med.*, 1982: 307:540–542.

Palmaz et al., "Removable Biliary Endoprosthesis," *AJR* 140: 812–814, Apr. 1983.

Coons et al., "Large–Bore, Long Biliary Endoprosthesis (Biliary Stents) for Improved Drainage." Radiology 148: 89–94 (Jul. 1983) (C13772–78).

Andrew Cragg, Gunnar Lund, Erich Salomonowitz, Joseph Rysavy, Flavio Castaneda, Wilfrido Castaneda–Zuniga, Kurt Amplatz, "A New Percutaneous Vena Cava Filter", *AJR* 141: pp. 601–604, Sep. 1983.

Karlan Jr., et al., "A Simple Method for Insertion of Large Untapered Catheters" *AJR* 141: 792 (Oct. 1983) (C13808).

Teplick et al., "A New Biliary Endoprosthesis" *AJR* 141: 799–801 (Oct. 1983) (C14097–14100).

Castaneda–Zuniga, Ed. "Transluminal Angioplasty," 1983. (C14281–328).

Roehm, Jr., et al., "Percutaneous Transcatheter Filter for the Inferior Vena Cava", *Radiology*, vol. 150, No. 1, pp. 255–257 (Jan. 1984).

Andrew H. Cragg, M.D., Gunnar Lund, M.D., Joseph A. Rysavy, B.A., Erich Salomonowitz, M.D., Wilfrido R. Castaneda–Zuniga, M.D., Kurt Amplatz, M.D., "Percutaneous Arterial Grafting", *Radiology*, vol. 150, No. 1, Jan. 1984, pp. 45–49. (C014108–113).

Kerlan, Jr. et al., "Biliary Endoprostheses, Insertion Using a Combined Peroral–Transhepatic Method," Radiology 1984; 150:828–830 (C14268–70).

Lund, et al., "A New Vena Cava Filter for Percutaneous Placement and Retrieval: Experimental Study", *Radiology*, vol. 152, No. 2, Aug., 1984, pp. 369–372.

Fogarty, T.J., Kinney, T.B.; Finn, J.C.: Current status of dilatation catheters and guiding instruments. *Am. J. Cardiol.*, 1984, 15; 53(12): 97C–101C.

Fogarty, T.J.; Kinney, T.B., Intraoperative Coronary artery balloon–catheter dilatation. *Am. Heart J.* 1984, 107(4):845–51.

Fogarty et al., "Intraoperative Coronary Artery Balloon–Catheter Dilation," *American Heart Surgery* 107: 845–51 (1984) (C14209–15).

Labadibi Z., Wu, R.J., Walls, T.J.: Percutaneous balloon aortic valvuloplasty: Results in 23 patients. *Am. J. Cardioi.* 1984; 53; 194.

Inoue, K., Owani, T. Nahamura, T. Et al., Clinical application of transmitral commissurotomy by a new balloon catheter. *J. Thorac. Cardiovascular Surg.* 1984; 87:394.

Rolf W. Gunther, M.D., Hans Schild, M.D., Axel Fries, S. Storkel, M.D., "Vena Caval Filter to Prevent Pulmonary Embolism: Experimental Study", *Radiology*, vol. 156, No. 2, Aug. 1985, pp. 315–320.

Donald F. Denny, John J. Cronan, Gary S. Dorfman, Cordell Esplin, "Percutaneous Kimray–Greenfield Filter Placement by Femoral Vein Puncture", AJR 145: pp. 827–829, Oct. 1985.

Chusilp Charnangevej, M.D., Sidney Wallace, M.D., Kenneth C. Wright, Ph.D., Humberto Carrasco, M.D., Cesare Gianturco, M.D., "Endovascular Stent for Use in Aortic Dissection: An in Vitro Experiment", *Radiology* 1985: vol. 157, pp. 323–324.

Papanicolaou, et al. "Insertion of a Biliary Endoprosthesis Using a Balloon Dilatation Catheter," Gastrointest. Radio. 10:394–96 (1985). (C013809–11).

Carrasco et al., "Expandable Biliary Endoprosthesis: An Experimental Study," *American Journal of Roentgenology*, 145 (1985), 1279–1281 (C013998–00).

Wallace et al, "Tracheobronchial Tree: Expandable Metallic Stents Used in Experimental and Clinical Applications," *Radiology* 1986; 158: 309–312 (Feb. 1986) (C13994–97).

Rosch et al., "Transjugular–Intraheptic Portacaval Shunt: An Experimental Work," *The American Journal of Surgery* 590–92 (C14575–77).

Kononov Discovery Deposition, Nov. 7–9, 17, 1996 (pp. 35–36, 41–43, 92–100, 122–125, 293–318, 455–457 redacted as confidential) Appendix V, Exhibit P)(Kononov Notebook).

Kononov Evidentiary Deposition, Nov. 18–19, 1996 (Appendix V, Exhibit P)(Kononov Notebook).

Cook's Supplemental Responses to JJIS Discovery Request Nos. 15, 19, 20, 23, 24 and 39 (Appendix IV, Exhibit I) (Kononov Notebook).

Coons Supplemental Report, pp. 1–3 and Exhibits B–E thereto (Appendix VI, Exhibit M) (Kononov Notebook).

Coons Deposition, pp. 70–82 and 99–100 (Appendix V, Exhibit F) (Kononov Notebook).

Gardner Deposition, pp. 168–227, 232–257 (Appendix V, Exhibit K) (Kononov Notebook).

Palmaz Deposition, Dec. 5, 1996, pp. 1837–1860 (Appendix V, Exhibit AA) (Kononov Notebook).

Wholey Deposition, pp. 148–175 (Appendix V, Exhibit KK) (Kononov Notebook).

Criado Deposition, pp. 101–116 (Appendix V, Exhibit G) (Lazarus Notebook).

Kononov Discovery Deposition, Nov. 7, 1996, pp. 83–100 (pp. 92–100 redacted) (Appendix V, Exhibit P) (Lazarus Notebook).

Kononov Discovery Deposition, Nov. 9, 1996, pp. 458–470 (Appendix V, Exhibit P) (Lazarus Notebook).

Kononov Evidentiary Deposition, Nov. 18–19, 1996, pp. 126–142 (Appendix V, Exhibit P) (Lazarus Notebook).

Deposition testimony of Julius G. Hammerslag, May 11, 1996 (Appendix V, Exhibit M) (Hammerslag Notebook).

Cook's Supplemental Answers to JJIS' Discovery Request Nos. 6, 18–23, 34 and 37. Responses to request Nos. 19, 21, 22, 23 (Appendix IV, Exhibit F) (Hammerslag Notebook).

Cook's Supplemental Responses to JJIS' Discovery Request Nos. 18, 22 and 23. (Appendix IV, Exhibit H) (Hammerslag Notebook).

Adelman Report, pp. 4–8, 15–16. (Appendix VI, Exhibit A) (Hammerslag Notebook).

Coons Report, pp. 1, 6–7, 18–24, and Exhibits B–E thereto (Appendix VI, Exhibit L) (Hammerslag Notebook).

Coons Supplemental Report, pp. 2–3, and Exhibits B–E thereto (Appendix VI, Exhibit M) (Hammerslag Notebook).

Goolkasian Report, pp. 4, 13–18 (Appendix VI, Exhibit U) (Hammerslag Notebook).

Harmon Report, pp. 3–4, 26–27 (Appendix VI, Exhibit V) (Hammerslag Notebook).

Segan Answering Report, pp. 6–8, 10–11 (Appendix VI, Exhibit FF) (Hammerslag Notebook).

Wholey Report, pp. 5–7, 9–10 (Appendix VI, Exhibit KK) (Hammerslag Notebook).

Beck Deposition, pp. 216–228 (Appendix V, Exhibit A) (Hammerslag Notebook).

Buller Deposition, pp. 401–429 (Appendix V, Exhibit D) (Hammerslag Notebook).

Coons Deposition, pp. 83–84 (Appendix V, Exhibit F) (Hammerslag Notebook).

Emhardt Deposition, pp. 418–431 (Appendix V, Exhibit I) (Hammerslag Notebook).

Gardner Deposition, pp. 239–252, 339–376, 440–444 (Appendix V, Exhibit K) (Hammerslag Notebook).

Hodgson Deposition, pp. 79–88 (Appendix V, Exhibit N) (Hammerslag Notebook).

Kula Deposition, pp. 630–635, 647–651 (Appendix V, Exhibit Q) (Hammerslag Notebook).

Lipow Deposition, pp. 77–78, 114–177, 206–229, 263–344 (Appendix V, Exhibit U) (Hammerslag Notebook).

Palmaz Deposition, Feb. 6, 1996, pp. 919–923 (Appendix V, Exhibit AA) (Hammerslag Notebook).

Palmaz Deposition, Apr. 16, 1996, pp. 1089–1112, 1252–1271 (Appendix V, Exhibit AA) (Hammerslag Notebook).

Tobor Deposition, pp. 280–297 (Appendix V, Exhibit II) (Hammerslag Notebook).

Wholey Deposition, pp. 207–239 (Appendix V, Exhibit KK) (Hammerslag Notebook).

Gianturco U.S. Patent No. 5,041,126 (Application No. 244,669) (Appendix VIII, Exhibit B1) (Hammerslag Notebook).

Office Action, dated Oct. 2, 1989 in Application S.N. 244,669, p. 2 (Appendix VIII, Exhibit B2) (Hammerslag Notebook).

Jun. 29, 1994 Memorandum by Raymond Mehler (Appendix VIII, Exhibit A1) (Hammerslag Notebook).

Jul. 11, 1994 letter from H. Collins, Patent Counsel at Cordis to D. Latham, Medtronics (Appendix VIII, Exhibit A2) (Hammerslag Notebook).

Jul. 14, 1994 letter from D. Latham, Senior Patent Attorney at Medtronics to D. Hall, Cordis Corporation (Appendix VIII, Exhibit A3) (Hammerslag Notebook).

U.S. Patent No. 4,969,458 (Appendix VIII, Exhibit C1) (Hammerslag Notebook).

Office Action in Application S.N. 69,636 dated Mar. 17, 1988, p. 3. (Appendix VIII, Exhibit C2) (Hammerslag Notebook).

Response to Office Action, pp. 4–8 (Appendix VIII, Exhibit C3) (Hammerslag Notebook).

JJIS' Memorandum of Law on the Interpretation of the Asserted Claims of the '665 Patents pp. 4–5, 20–23 (Appendix VII, Exhibit A) (Ersek Notebook).

JJIS' Reply Memorandum of Law on the Interpretation of the Asserted Claims of the '665 Patent, pp. 30–33 (Appendix VII, Exhibit C) (Ersek Notebook).

Frenchick Deposition, JJIS 30(b)(6) witness on infringement, pp. 472–486 (Appendix V, Exhibit J) (Ersek Notebook).

Cook's Supplemental Responses to JJIS' Discovery Request Nos. 15, 19, 20, 23, 24 and 39, pp. 6–8 (Appendix IV, Exhibit I) ) (Ersek Notebook).

Adelman Report, pp. 7–8, 10–11, 16 (Appendix VI, Exhibit A) (Ersek Notebook).

Andros Report, entire document (Appendix VI, Exhibit B) (Ersek Notebook).

Collins Answering Report, entire document (Appendix VI, Exhibit J) (Ersek Notebook).

Coons Report, pp., 8, 18–24, Exhibits B–3 (Appendix VI, Exhibit L) (Ersek Notebook).

Coons Supplemental Report, p. 3, Exhibits B–E (Appendeix VI, Exhibit M) (Ersek Notebook).

Gardner Report, pp. 29–34 (Appendix VI, Exhibit S) (Ersek Notebook).

Goolkasian Report, pp. 2–3, 19–25, (Appendix VI, Exhibit U) (Ersek Notebook).

McIntosh Report, entire document (Appendix VI, Exhibit BB) (Ersek Notebook).

Segal Answering Report, pp. 6–8 (Appendix VI, Exhibit FF) (Ersek Notebook).

Wholey Report, pp. 6–10, 15–18 (Appendix VI, Exhibit KK) (Ersek Notebook).

Buller Deposition, pp. 354–360, 396–401 (Appendix V, Exhibit D) (Ersek Notebook).

Collins Deposition, pp. 59–95, 107–126 (Appendix V, Exhibit E) (Ersek Notebook).

Criado Deposition, Mar. 5, 1996, pp. 62–100, 126–143, 148–158, 170–172, 225–279 (Appendix V, Exhibit G) (Ersek Notebook).

Cumberland Deposition, pp. 25–27, 64–72 (Appendix V, Exhibit H) (Ersek Notebook).

Gardner Deposition, Dec. 18–19, 1996, pp. 162–170, 239–250, 429–440 (Appendix V, Exhibit K) (Ersek Notebook).

Hammerslag Deposition, pp. 74–75, 86–89 (Appendix V, Exhibit M) (Ersek Notebook).

Hodgson Deposition, Dec. 5, 1996, pp. 43–54, 57–78, 86–91, 112–163, 171–178, 188–211 (Appendix V, Exhibit N) (Ersek Notebook).

Kononov Discovery Deposition, Nov. 9, 1996, pp. 465–468 (Appendix V, Exhibit P) (Ersek Notebook).

Kononov Evidentiary Deposition, Nov. 18, 19, 1996, pp. 92–96, 204–205, 208–224, 246–252 (Appendix V, Exhibit P) (Ersek Notebook).

Kula Deposition, Apr. 10, 1996, pp. 626–743 (Appendix V, Exhibit Q) (Ersek Notebook).

Leewood Deposition, pp. 63–77, 232–239, 241–246 (Appendix V, Exhibit S) (Ersek Notebook).

Lipow Deposition, Mar. 12, 1996, pp. 51–55, 120–122, 206–213 (Appendix V, Exhibit U) (Ersek Notebook).

Lipow Deposition, Mar. 13, 1996, pp. 374–386, 547–562 (Appendix V, Exhibit U) (Ersek Notebook).

Lipow Deposition, Mar. 14, 1996, pp. 572–605, 617–625, 643–644 (Appendix V, Exhibit U) (Ersek Notebook).

McIntosh Depositon, pp. 4–91, 103–197 (Appendix V, Exhibit V) (Ersek Notebook).

Palmaz Deposition, Apr. 16, 1996, pp. 1206–1232 (Appendix V, Exhibit AA) (Ersek Notebook).

Palmaz Deposition, Dec. 5, 1996, pp. 1777–1781 (Appendix V, Exhibit AA) (Ersek Notebook).

Palmaz Testimony, Dec. 5, 1991, pp. 11–24 (Appendix X, Exhibit B) (Ersek Notebook).

Palmaz Testimony, Dec. 6, 1991, pp. 32–63 (Appendix X, Exhibit B) (Ersek Notebook).

Tio Deposition, pp. 431–438 (Appendix V, Exhibit HH) (Ersek Notebook).

Tobor Deposition, Oct. 11, 1995, pp. 155–162, 189–236 (Appendix V, Exhibit II) (Ersek Notebook).

Tobor Deposition, May 1, 1996, pp. 684–723 (Appendix V, Exhibit II) (Ersek Notebook).

Tobor Deposition, Tobor, May 2, 1996, pp. 884–915 (Appendix V, Exhibit II) (Ersek Notebook).

Waller Deposition, pp. 32–33, 183–193, 206–244 (Appendix V, Exhibit JJ). (Ersek Notebook).

Wholey Deposition, Dec. 7, 1996, pp. 119–148, 175, 183–184 (Appendix V, Exhibit KK) (Ersek Notebook).

Windeler Testimony, Oct. 11, 1991, pp. 60–78, 99–103 (Appendix X, Exhibit C) (Ersek Notebook).

Affidavit of Erik K. Antonsson, Ph.D., P.E., C35148–84 (Appendix VIII, Exhibit G) (Ersek Notebook).

Petition to Reissue (Mar. 17, 1995) (Canada) (Appendix II, Exhibit K) (Ersek Notebook).

Decision of the Technical Board of Appeal (2 Apr. 1996) (EPO) (Appendix II, Exhibit R), (Ersek Notebook).

Minutes of the Oral Proceedings (2 Apr. 1996) (EPO) (Appendix II, Exhibit S) (Ersek Notebook).

Reply to Official Communication dated Oct. 6, 1989 (31 Jan. 1990) (EPO) (Appendix II, Exhibit HH) (Ersek Notebook).

Amendment and Argument in Japanese Application No. 225376/91 (Dec. 11, 1996)(Appendix II, Exhibit MM) (Ersek Notebook).

Notification from Japanese Patent Office Regarding Document filed by Third Party to Reject Japanese Application No. 225376/91 (Aug. 20, 1996) (Appendix II, Exhibit OO) (Ersek Notebook).

Letter from John & Kernich requesting surrender of South African Patent No. 86/8414 (Aug. 5, 1996)(Appendix II, Exhibit UU) (Ersek Notebook).

Submission of New Claims (Mar. 19, 1990) (EPO) (Appendix II, Exhibit KKK) (Ersek Notebook).

Communication of European Search Report (Jul. 13, 1989) (Appendix II, Exhibit LLL) (Ersek Notebook).

Submission by Third Party to Japanese Patent Office (Jun. 14, 1996) (Appendix II, Exhibit MMM) (Ersek Notebook).

Response to May 13, 1994 Communication (Nov. 4, 1994) (EPO) (Appendix II, Exhibit QQQ) (Ersek Notebook).

Communication (May 13, 1994) (EPO) (Appendix II, Exhibit RRR) (Ersek Notebook).

Response to Second Official Report (Oct. 19, 1994) (Australia) (Appendix II, Exhibit TTT) (Ersek Notebook).

Second Official Report (Mar. 10, 1994) (Australia) (Appendix II, Exhibit UUU) (Ersek Notebook).

Response to First Official Report (Feb. 22, 1994) (Australia) (Appendix II, Exhibit VVV) ) (Ersek Notebook).

First Official Report (Feb. 23, 1993) (Australia) (Appendix II, Exhibit WWW) (Ersek Notebook).

Response to Official Report (Sep. 5, 1996) (Australia) (Appendix II, Exhibit YYY) (Ersek Notebook).

Official Report (Feb. 19, 1996 ) (Australia) (Appendix II, Exhibit ZZZ) (Ersek Notebook).

Statements Submitted to EPO by Opposer (18 Mar. 1996) (Appendix II, Exhibit T) (Ersek Notebook).

Notice of issues to be Addressed at Oral Proceedings (27 Feb. 1996) (EPO) (Appendix II, Exhibit U) (Ersek Notebook).

Brief Submitted by Opposer (18 Jan. 1996) (EPO) Appendix II, Exhibit V) (Ersek Notebook).

Patentee Submission of Amended Claims and Statement of Arguments (20 Jan. 1995) (EPO) (Appendix II, Exhibit W) (Ersek Notebook).

Brief Submitted by Opposer (11 Jul. 1995) (EPO) (Appendix II, Exhibit X) (Ersek Notebook).

Statement of Grounds of Appeal (22 Nov. 1993) (EPO) (Appendix II, Exhibit Y) (Ersek Notebook).

Revocation of European Patent (12 Jul. 1993) (EPO) (Appendix II, Exhibit Z) (Ersek Notebook).

Brief Submitted by Opposer (17 May 1993) (EPO) (Appendix II, Exhibit AA) (Ersek Notebook).

Response to Official Communication dated Nov. 8, 1991 (EPO) (17 Aug. 1992 ) (Appendix II, Exhibit BB) (Ersek Notebook).

Notice of Opposition by Advanced Surgical Intervention Inc. (30 Oct. 1991) (EPO) (Appendix II, Exhibit CC) (Ersek Notebook).

Notice of Opposition by Boston Scientific Corp. (30 Jan. 1991 ) (EPO) Appendix II, Exhibit DD) (Ersek Notebook).

Translation of Submission by Third Party Trial–Demanding Brief (Nov. 8, 1996) (Japan) (Appendix II, Exhibit NN) (Ersek Notebook).

Patrick W. Serruys, Rotterdam, Thoraxcentre Interventional Cardiology Group, Handbook of Coronary Stents, 1997.

Brief of Terumo Kobushiki Kaisha to Invalidate Patent, Nov. 8, 1996 (Appendix II, Exhibit AAAA) (Esek Notebook).

Reply to Patent Opposition and Request for Amendment, Sep. 25, 1997 (Appendix II, Exhibit BBBB) (Ersek Notebook).

Declaration of Lee P. Bendel.

Affidavit of Julio C. Palmaz.

Declarationof Marvin L. Woodall.

Expert Report of Dr. Nigel Pearson Buller.

Petition To Revoke European Patent No. 0 221 570 (UK) (13 Mar. 1997).

Amended Particulars Of Objections (European Parent No. 0 221 570 (UK) (27 Oct. 1997).

Plea of Invalidity Of EP Patent 0 221 570 B1 (Italy) (21 Mar. 1997).

Writ Of Summons In Nullity By Boston Scientific Of European patent Nos. 0 221 570 And 0 335 341 (France) (17 Mar. 1997).

Writ Of Summons On Nullity By Saint–Come Of European Patent 0 221 570 B1 (France) (12 Mar. 1997).

Brief Of Response Submitted By Dr. Palmaz (France) (23 Oct. 1997).

English Translation Of Certain Portions Of Nullity Action By Biotronik Against European Patent No. 0 221 570 (Appendix II, Exhibit Q).

Plea Of Invalidity Of European Patent No. 0 221 570 By Boston Scientific (Netherlands) (13 Mar. 1997).

Memorandum Of Oral Pleading Filed On Behalf Of Boston Scientific (Netherlands) (12 Sep. 1997).

Plea Notes Filed On Behalf Of Palmaz (Netherlands) 12 Sep. 1997).

Provisional Judgment Of District Court In The Hague (Netherlands) (29 Oct. 1997).

Arterial Vascular Engineering, Inc.'s "Complaint For Declaratory Relief Of Patent Invalidity, Unenforceability, Noninfringement, And For Antitrust Violations", Case No. 97–700, Dec. 26, 1997.

Cordis Corporation's "Complaint For Patent Infringement And Demand For Jury Trial", Case No. 97–550, Oct. 3, 1997.

Cordis Corporation's "First Amended Complaint And Demand For Jury Trial", Case No. 97–550–SLR, Oct. 21, 1997.

Boston Scientific Corporation and SCIMED Life System, Inc.'s "Answer", Case No. 97–550–SLR, Nov. 12, 1997.

Cordis Corporation's "Cordis's Motion For A Preliminary Injunction Against Arterial Vascular Engineering, Inc.", Case No. 97–550–SLR, Dec. 29, 1997.

Cordis Corporation's "Cordis Corporation's Motion For a Preliminary Injunction", Case No. 97–550, Oct. 8, 1997.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 7, after line 20:

*With reference to FIGS. 1A and 1B, it is seen that certain of the slots 82 formed in tubular member 71 are open ended slots. The circumferentially adjacent slots 82, whether open ended or closed, define ring portions that are defined by a plurality of peak portions and valley portions. In the preferred embodiment, the ring portions at the first and second ends 72, 73 are not in phase with each other. Also in the preferred embodiment, open ended slots are defined by a pair of spaced apart elongate members 75 that are connected together by a connecting member 77 that extends between one end of each of the elongate members 75.*

AS A RESULT OF REEXAMINATION, IT HAS BEEN DETERMINED THAT:

The patentability of claims 23 and 34 is confirmed.

Claims 13 and 24 are cancelled.

Claims 1, 14, 16–19, 25, 29, 31–33, 35, 37, 40 and 41 are determined to be patentable as amended.

Claims 2–12, 15, 20–22, 26–28, 30, 36, 38, 39, 42 and 43, dependent on an amended claim, are determined to be patentable.

New claims 44–59 are added and determined to be patentable.

1. A method for implanting a prosthesis within a body passageway comprising the steps of:
   utilizing a thin-walled, tubular member as the prosthesis, the tubular member having a plurality of slots formed therein, the slots being disposed substantially parallel to the longitudinal axis of the tubular member;
   disposing the prosthesis upon a catheter;
   inserting the prosthesis and catheter within the body passageway by catheterization of said body passageway; and
   expanding and deforming the prosthesis at [a desired] *the location of an existing natural obstruction* within the body passageway by expanding a portion of the catheter associated with the prosthesis to force the prosthesis radially outwardly into contact with the body passageway, the prosthesis being deformed beyond its elastic limit.

14. The expandable intraluminal vascular graft of claim [13] *23*, wherein the slots are uniformly and circumferentially spaced from adjacent slots and the slots are uniformly spaced from adjacent slots along the longitudinal axis of the tubular member, whereby at least one elongate member is formed between adjacent slots.

16. The expandable intraluminal vascular graft of claim [13] *23*, wherein the tubular member does not exert any outward, radial force while the tubular member has the first or second, expanded diameter.

17. The expandable intraluminal vascular graft of claim [13] *23*, wherein the slots have a substantially rectangular configuration when the tubular member has the first diameter; and the slots have a substantially hexagonal configuration when the tubular member has the second, expanded diameter.

18. The expandable intraluminal vascular graft of claim [13] *23*, wherein the slots have a configuration which is substantially a parallelogram after the tubular member has been expanded and deformed into the second expanded diameter.

19. The expandable intraluminal vascular graft of claim [13] *23*, wherein the tubular member has a biologically inert coating on the wall surface.

25. The expandable prosthesis for a body passageway of claim [24] *34*, wherein the tubular member has a biological inert coating on the wall surface.

29. The expandable prosthesis of claim [24] *34*, wherein the slots are uniformly and circumferentially spaced from adjacent slots and the slots are uniformly spaced from adjcent slots along the longitudinal axis of the tubular member, whereby at least one elongate member is formed between adjacent slots.

31. The expandable prosthesis of claim [24] *34*, wherein the tubular member does not exert any outward, radial force while the tubular member has the first or second expanded diameter.

32. The expandable prosthesis of claim [24] *34*, wherein the slots have a substantially rectangular configuration when the tubular member has the first diameter, and the slots have a substantially hexagonal configuration when the tubular member has the second, expanded diameter.

33. The expandable prosthesis of claim [24] *34*, wherein the slots have a configuration which is substantially a parallelogram after the tubular member has been expanded and deformed intop the second expanded diameter.

35. An apparatus for intraluminally reinforcing a body passageway, comprising:
   an expandable and deformable, thin-walled tubular prosthesis having first and second ends, and a wall surface disposed between the first and second ends, the wall surface having a *substantially uniform thickness and a* plurality of slots formed therein, the slots being disposed substantially parallel to the longitudinal axis of the prosthesis, *the prosthesis having a first diameter which permits intraluminal delivery of the prosthesis into a body passageway having a lumen and wherein the outside of the wall surface of the prosthesis is a smooth surface when the prosthesis has the first diameter;* and
   a catheter having an expandable, inflatable portion associated therewith and including means for mounting and retaining the expandable, thin-walled tubular prosthesis on the expandable, inflatable portion,
   whereby upon inflation of the expandable, inflatable portion of the catheter, the prosthesis is expanded and deformed radially outwardly into contact with the body passageway.

37. An apparatus for expanding the lumen of a body passageway comprising:
   an expandable and deformable thin-walled intraluminal vascular graft having first and second ends, and a wall surface disposed between the first and second ends, the wall surface having a *substantially uniform thickness and a* plurality of slots formed therein, the slots being disposed substantially parallel to the longitudinal axis of the graft, *the vascular graft having a first diameter which permits intraluminal delivery of the graft into a body passageway having a lumen and wherein the outside of the wall surface of the graft is a smooth surface when the graft has the first diameter;* and a catheter having an expandable, inflatable portion associated therewith and including means for mounting and retaining the expandable, deformable intraluminal vascular graft on the expandable, inflatable portion, whereby upon inflation of the expandable, inflatable portion of the catheter, the intraluminal vascular graft is expanded and deformed radially outwardly into contact with the body passageway.

40. The expandable intraluminal vascular graft of claim [13] 23, wherein tantalum is utilized for the tubular member.

41. The expandable prosthesis of claim [24] 34, wherein tantalum is utilized for the tubular member.

44. A method for implanting a balloon expandable stent prosthesis within a passageway of a coronary artery having an area of stenosis, comprising the steps of:

utilizing a thin-walled, tubular member as the stent prosthesis, the tubular member having a plurality of slots formed therein, the slots being disposed substantially parallel to the longitudinal axis of the tubular member;

disposing the stent prosthesis upon a catheter having an inflatable balloon portion;

inserting the stent prosthesis and catheter within the passageway by percutaneous catheterization;

delivering the catheter and stent prosthesis to the area of stenosis without surgically exposing the area of the passageway; and expanding and deforming the stent prosthesis at the area of stenosis within the coronary artery passageway by expanding the inflatable balloon portion of the catheter associated with the stent prosthesis to force the stent prosthesis radially outwardly into contact with the area of stenosis in the passageway, the stent prosthesis being controllably deformed beyond its elastic limit.

45. The method of claim 44 wherein at least certain of the slots are defined by a pair of spaced apart elongate members that are connected together at one end of each of the elongate members so as to define an open ended slot.

46. The method of claim 44, wherein said tubular member includes at least one ring portion defined by circumferentially adjacent slots so as to define a plurality of peak portions and valley portions.

47. The method of claim 46, wherein said tubular member has a first end and a second end and includes one of said ring portions at said first and second ends thereof.

48. The method of claim 46, wherein the tubular member is formed from a plastically deformable material.

49. The method of claim 46, wherein the stent prosthesis after expansion has mechanical strength sufficient to provide radial support of the body passageway and prevent migration of the stent prosthesis within the body passageway.

50. The method of claim 46, wherein the tubular member has an outer wall surface and the slots formed in the outer wall surface upon expansion of the tubular member define open areas of approximately eighty percent (80%) of the area of the wall surface.

51. In combination, a balloon expandable stent prosthesis for implantation in the passageway of a coronary artery having an area of stenosis and a catheter, comprising:

an expandable stent prosthesis being a thin-walled tubular member having first and second ends and a wall having an outer wall surface disposed between the first and second ends, the wall having a substantially uniform thickness and a plurality of slots formed therein, the slots being disposed substantially parallel to the longitudinal axis of the tubular member;

a catheter having an expandable, inflatable balloon portion;

the tubular member being disposed on the balloon portion of the catheter;

the tubular member having a first diameter which permits intraluminal delivery of the tubular member and the catheter into a lumen of a coronary artery having an area of stenosis and wherein the outside of the wall surface of the tubular member is a smooth surface when the tubular member has the first diameter; and the tubular member having a second, expanded and deformed diameter upon the application from the interior of the tubular member of radially, outwardly extending force, by inflating the balloon portion of the catheter, which second diameter is variable and controlled by the amount of force applied to the tubular member, whereby the tubular member may be expanded and deformed to expand the coronary artery in the area of stenosis.

52. The combination of claim 51, wherein at least certain of the slots are defined by a pair of spaced apart elongate members that are connected together at one end of each of the elongate members so as to define an open ended slot.

53. The combination of claim 52, wherein a connecting member extends between and connects said one end of each of the elongate strut members.

54. The combination of claim 51, wherein said tubular member includes at least one ring portion defined by circumferentially adjacent slots so as to define a plurality of peak portions and valley portions.

55. The combination of claim 54, wherein said tubular member includes one of said ring portions at its first and second ends.

56. The balloon expandable stent prosthesis of claim 55, wherein the ring portions at the first and second ends are not in phase with each other.

57. The combination of claim 51, wherein the tubular member is formed of a plastically deformable material.

58. The combination of claim 51, wherein the tubular member in its second, expanded diameter has mechanical strength sufficient to provide radial support of the coronary artery and prevent migration of the tubular member from the area of stenosis.

59. The combination of claim 51, wherein the slots formed in the wall surface of the tubular member in its second, expanded diameter define open areas of approximately eighty percent (80%) of the area of the wall surface.

* * * * *

(12) EX PARTE REEXAMINATION CERTIFICATE (6582nd)
United States Patent
Palmaz

(10) Number: US 4,739,762 C2
(45) Certificate Issued: Dec. 23, 2008

(54) EXPANDABLE INTRALUMINAL GRAFT, AND METHOD AND APPARATUS FOR IMPLANTING AN EXPANDABLE INTRALUMINAL GRAFT

(75) Inventor: Julio C. Palmaz, San Antonio, TX (US)

(73) Assignee: Cordis Corporation, Miami, FL (US)

Reexamination Request:
No. 90/007,627, Jul. 13, 2005
No. 90/008,780, Jul. 26, 2007
No. 90/008,797, Aug. 9, 2007

Reexamination Certificate for:
Patent No.: 4,739,762
Issued: Apr. 26, 1988
Appl. No.: 06/923,798
Filed: Nov. 3, 1986

Reexamination Certificate B1 4,739,762 issued Oct. 27, 1998

Related U.S. Application Data

(63) Continuation-in-part of application No. 06/796,009, filed on Nov. 7, 1985, now Pat. No. 4,733,665.

(51) Int. Cl.
*A61F 2/06* (2006.01)
*A61M 29/00* (2006.01)

(52) U.S. Cl. ............... 623/1.11; 604/104; 604/96.01; 623/1.46

(58) Field of Classification Search ............... None
See application file for complete search history.

(56) References Cited

U.S. PATENT DOCUMENTS

| | | | | |
|---|---|---|---|---|
| 3,657,744 A | * | 4/1972 | Ersek | 128/898 |
| 4,512,338 A | * | 4/1985 | Balko et al. | 606/108 |
| 4,553,545 A | * | 11/1985 | Maass et al. | 606/198 |
| 4,560,374 A | * | 12/1985 | Hammerslag | 604/509 |

OTHER PUBLICATIONS

Ersek, Robert A., "Expandible Metal Mesh Cylinder for Replacement of Aortic Valve", Notice of Research Project—American Heart Association, Dec. 31, 1969.*

Monograph prepared by Dr. Palmaz—dated 1980.*

Monograph prepared by Dr. Palmaz—dated May 18, 1983.*

Selected pages from depositions of various witnesses that relate to 1980 and 1983 monographs.

*Johnson & Johnson Inc., et al. v. Boston Scientific Ltd., et al.*, Judment in the Federal Court, Canada, Apr. 30, 2008 (Case No. T–1822–97).

*Johnson & Johnson Inc., et al. v. Boston Scientific Ltd., et al.*, collection of the final testimony of various witnesses (Case No. T–1822–97).

*Cordis Corp. v. Boston Scientific Corp. et al.*, Opening Brief in Support of BSC's Motion for Summary Judgment of Invalidity of the Asserted Claims of the Palmaz '762 patent, Apr. 1, 2005 (Civil Action No. 03–27–SLR).

*Cordis Corp. v. Boston Scientific Corp. et al.*, Memorandum Opinion, Jun. 3, 2005 (Civil Action No. 03–27–SLR).

*Cordis Corp. v. Boston Scientific Corp. et al.*, Cordis' Brief Opposing BSC's Motion for Summary Judgment of Invalidity of the Asserted Claims of the Palmaz '762 patent, Apr. 14, 2005 (Civil Action No. 03–27–SLR).

*Cordis Corp. v. Boston Scientific Corp. et al.*, BSC's Reply Brief in Support of its Motion for Summary Judgment of Invalidity of the Asserted Claims of the Palmaz '762 patent, Apr. 1, 2005 (Civil Action No. 03–27–SLR).

(Continued)

*Primary Examiner*—Beverly M. Flanagan

(57) ABSTRACT

An expandable and deformable intraluminal vascular graft is expanded within a blood vessel by an angioplasty balloon associated with a catheter to dilate and expand the lumen of a blood vessel. The graft may be a thin-walled tubular member having a plurality of slots disposed substantially parallel to the longitudinal axis of the tubular member.

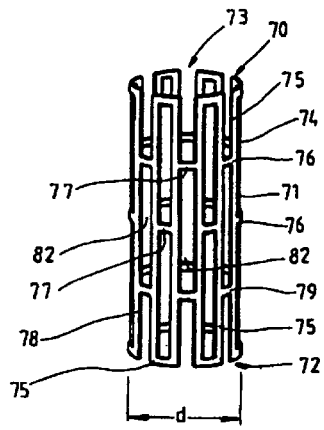
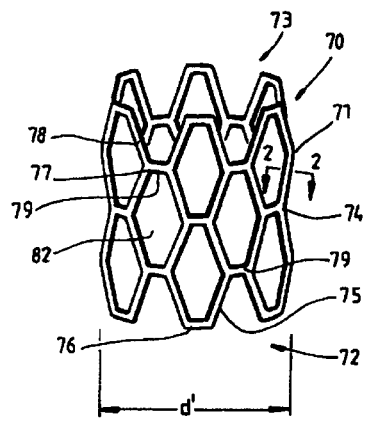

OTHER PUBLICATIONS

*Cordis Corp. v. Boston Scientific Corp. et al.,* Cordis' Answering Brief in Opposition to BSC's Motion for Summary Judgment of Invalidity of the Asserted Claims of the Palmaz '762 patent, Apr. 21, 2005 (Civil Action No. 03–27–SLR).

The University of Texas Health Science Center at San Antonio Invention Report, Expandable Intraluminal Graft, Julio Cesar Palmaz, Aug. 9, 1984.

Palmaz disclosures prior to Nov. 7, 1984 (e.g., disclosures of 1980 Monograph, 1983 Monograph, and revisions thereof).

Prior use of stents, including neurological applications and Palmaz' implantations (public uses) of stent prior to Nov. 7, 1984.

Various balloon catheters in existence prior to the filing of the '665 patent, including the BlueMax Balloon Dilation Catheters from Medi–Tech, the Trac, the Trac Plus, the Mills Operative Angioplasty, the Mills Operative Coronary Angioplasty, the ACS Low–Profile Steerable Coronary Balloon Dilation Catheter, the Hartzler LPS Coronary Balloon Dilation Catheter, the Simpson Ultra–Low Profile Coronary Balloon Dilation Catheter. (See, e.g., balloon catheters discussed in Blue Max Catheter brochure from 1985/Cook Incorporated Catalog 1982–84, Diagnostic & Interventional Products at 65–66; USCI Division, C.R. Bard, Inc. Hospital Price List (Effective Apr. 15, 1984); "Angioplasty Equipment and Supplies: Technical Considerations" at pp. 93 & 126, from Ch. 7 of the book "Practice of Coronary Angioplasty" (Ischinger, ed. 1986); Topol et al., "Selection of dilation hardware for ptca–1985," *Catherization and Cardiovascular Diagnosis* 11(6): 629–637 (1985)).

Abele, "Balloon Catheters and Transluminal Dilatation: Technical Considerations," AJR 135:901–906 (Nov. 1980).

Percutaneous Transluminal Angioplasty, Ch. 8, pp. 31–36, "Basic Technology of Balloon Catheters," by Abele (1983).

Bernhard, "Higher Balloon Dilatation Pressure in Coronary Angioplasty," *American Heart Journal,* 619–20 (Apr. 1984).

Chuang, "Nonoperative Retrieval of Gianturco Coils from Abdominal Aorta," AJR 132:996–997 (Jun. 1979).

Chuang, "Complications of Coil Embolization: Prevention and Management," AJR 137:809–813 (Oct. 1981).

Coons, H., et al., "Large–Bore, Long Biliary Endoprostheses (Biliary Stents) for Improved Drainage," Radiology 148:89–94 (1983).

Cragg A. et al., Transluminal Expandable Nitinol Coil Stent Grafting, Radiology 147:261–263 (Apr. 1983).

Dotter, "Transluminally Placed Coil–Spring Endarterial Tube Grafts: Long–Term Patency in Canian Popliteal Artery," *Invest. Radiol.* 4:329–32 (1969).

Dotter et al., "Transluminal Expandable Nitinol Coil Stent Grafting:Preliminary Report," *Radiology* 147:259–260 (Apr. 1983).

Fellows, "Therapeutic Catheter Procedures in Congenital Heart Disease:Current Status and Future Prospects," *Cardiovasc Intervent Radiol* 7:170–177 (Jun. 1984).

Glanz et al., "Stenotic Lesions in Dialysis–access Fistulas: Treatment by Transluminal Angioplasty Using High Pressure Balloons," *Radiology*156:236 (Jul. 1985).

Gruntzig, "Technique of Percutaneous Transluminal Angioplasty with the Gruntzig Balloon Catheter," *AJR* 132:547–552 (Apr. 1979).

Gruentzig, "Percutaneous transluminal coronary angioplasty," *Seminarsin Roentgenology,* 16:152–153 (Apr. 1981).

Harries–Jones, E., et al., "Repositioning of Biliary Endoprosthesis with Gruntzig Balloon Catheters," AJR 138:771–772 (1982).

Honickman, S., et al., "Malpositioned Biliary Endoprosthesis: Retrieveal Using a Vascular Balloon Catheter," Radiology 144:423–425 (1982).

Kerlan, R. et al., "Biliary Endoprostheses—Insertion Using a Combined Peroral–Transhepatic Method," Radiology 150:828–830 (1984).

Lary et al., "The Experimental Use of Steel Mesh Tubes for the Replacement of Arterial Segments," AMA Archives of Surgery 72:69–75 (Jan. 1956).

Maass et al., "Radiological Follow–up of Transluminally Inserted Vascular Endoprostheses: An Experimental Study Using Expanding Spirals," Radiology 152:659–663 (1984).

Percutaneous Transluminal Angioplasty, Ch. 9, pp. 37–45, "Dilatation and the Expanding Balloon Catheter. Advantages of the Expanding Balloon Catheter," by Olbert et al. (1983).

Program Abstract for the Nov. 1984 Annual Meeting of the Radiological Society of North America: Palmaz et al., "Expandable Intraluminal Graft: A Preliminary Study," (Oct. 1984).

Papanicolaou, N., et al., "Insertion of a Biliary Endoprosthesis Using a Balloon Dilation Catheter," Gastrointestinal Radiology 10:394–396 (1985).

Simpson, "A New Catheter System for Coronary Angioplasty," *The American Journal of Cardiology* at 49:1216–1222 (Apr. 1982).

Teplick et al., "Management of Obstructed Biliary Endoprostheses" CardioVascular and Interventional Radiology 8:164–167 (May 1985).

Prior art cited in the file histories for the '665 patent and itsreexamination files.

Wright et al., "Percutaneous Endovascular Stents: An Experimental Evaluation," Radiology 156:69–72 (Jul. 1985).

*Cordis Corp. v. Boston Scientific Corp. et al.,* Appeal Brief for Defendants–Cross–Appellants, Court of Appeals for the Federal Circuit, May 12, 2008 (Appeal Nos. 208–1003,–1072).

*Cordis Corporation v. Boston Scientific Corp., and Scimed Life Systems, Inc.,* Response and Reply Brief for Plaintiff–Appellant Cordis Corporation, Court of Appeals for the Federal Circuit, Aug. 22, 2008 (Appeal Nos. 2008–1003,–1072).

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–12, 14–23, 25–44, 51 and 54 is confirmed.

Claims 13 and 24 were previously cancelled.

Claims 45–50, 52, 53 and 55–59 were not reexamined.

\* \* \* \* \*

(12) EX PARTE REEXAMINATION CERTIFICATE (6806th)
United States Patent
Palmaz

(10) Number: US 4,739,762 C3
(45) Certificate Issued: May 5, 2009

(54) EXPANDABLE INTRALUMINAL GRAFT, AND METHOD AND APPARATUS FOR IMPLANTING AN EXPANDABLE INTRALUMINAL GRAFT

(75) Inventor: Julio C. Palmaz, San Antonio, TX (US)

(73) Assignee: Cordis Corporation, Miami, FL (US)

Reexamination Request:
No. 90/010,119, Mar. 10, 2008
No. 90/010,287, Sep. 19, 2008

Reexamination Certificate for:
Patent No.: 4,739,762
Issued: Apr. 26, 1988
Appl. No.: 06/923,798
Filed: Nov. 3, 1986

Reexamination Certificate B1 4,739,762 issued Oct. 27, 1998

Reexamination Certificate C2 4,739,762 issued Dec. 23, 2008

Related U.S. Application Data

(63) Continuation-in-part of application No. 06/796,009, filed on Nov. 7, 1985, now Pat. No. 4,733,665.

(51) Int. Cl.
*A61F 2/06* (2006.01)
*A61M 29/00* (2006.01)

(52) U.S. Cl. .................... 623/1.11; 604/104; 604/96.01; 623/1.46

(58) Field of Classification Search .................. None
See application file for complete search history.

(56) References Cited

U.S. PATENT DOCUMENTS 3,570,014 A * 3/1971 Hancock
4,195,637 A * 4/1980 Gruntzig et al. ............. 604/509
4,343,048 A * 8/1982 Ross et al.

OTHER PUBLICATIONS

Monograph prepared by Dr. Palmaz—dated 1980.*
Monograph prepared by Dr. Palmaz—dated May 18, 1983.*
K. Nuesch, Y. Scholer, R. Pyle, Grüntzig, "Percutaneous Transluminal Dilatation of Proximal Stenosis of Left Anterior Descending Coronary Artery in Patient with Bronchogenic Carcinoma", BR Heart J. 1981; 46; 345–7.*
1980 Monograph by Dr. Palmaz.*
1983 Monograph by Dr. Palmaz.*
Gruntzig A., Klimpe D.A., "Technique of Percutaneous Transluminal Angioplasty With the Gruntzig Balloon–Catheter," AJR, Apr. 1979, 132: 547–552.*
K. Nuesch, Y. Scholer, R. Pyle, A. Gruntzig, "Percutaneous Transluminal Dilatation of Proximeal Stenosis of Left Anterior Descending Artery in Patient With Bronchogenic Carcinoma," Br Heart J. 1981; 46; 345–7.*
Selected pages from depositions of various witnesses that relate to 1980 and 1983 monographs.
*Johnson & Johnson Inc., et al. v. Boston Scientific, Ltd., et al.*, Judgment in the Federal Court, Canada, Apr. 30, 2008 (Case No. T–1822–97).
*Johnson & Johnson Inc., et al. v. Boston Scientific Ltd., et al.*, collection of the final testimony of various witnesses (Case No. T–1882–97).
*Cordis Corp. v. Boston Scientific Corp. et al.*, Opening Brief in Support of BSC's Motion for Summary Judgment of Invalidity of the Asserted Claims of the Palmaz '762 patent, Apr. 1, 2005 (Civil Action No. 03–27–SLR).
*Cordis Corp. v. Boston Scientific Corp. et al.*, Memorandum Opinion, Jun. 3, 2005 (Civil Action No. 03–27–SLR).
*Cordis Corp. v. Boston Scientific Corp. et al.*, Cordis' Brief Opposing BSC's Motion for Summary Judgment of Invalidity of the Asserted Claims of the Palmaz '762 patent, Apr. 14, 2005 (Civil Action No. 03–27–SLR).

(Continued)

*Primary Examiner*—Beverly M. Flanagan

(57) ABSTRACT

An expandable and deformable intraluminal vascular graft is expanded within a blood vessel by an angioplasty balloon associated with a catheter to dilate and expand the lumen of a blood vessel. The graft may be a thin-walled tubular member having a plurality of slots disposed substantially parallel to the longitudinal axis of the tubular member.

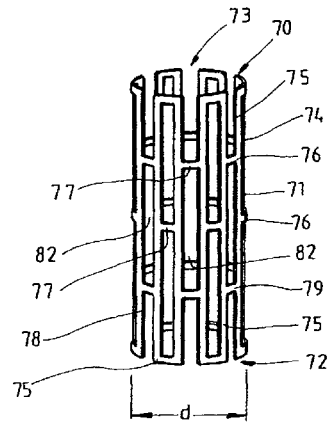
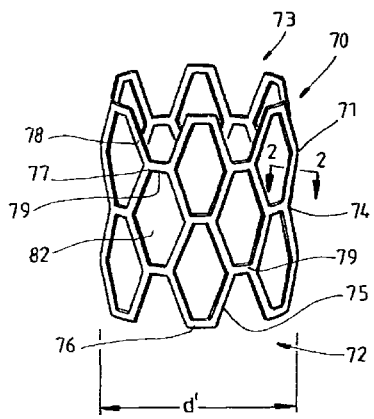

OTHER PUBLICATIONS

*Cordis Corp.* v. *Boston Scientific Corp. et al.*, BSC's Reply Brief in Support of its Motion for Summary Judgment of Invalidity of the Asserted Claims of the Palmaz '762 patent, Apr. 1, 2005 (Civil Action No. 03–27–SLR).

*Cordis Corp.* v. *Boston Scientific Corp. et al.*, Cordis' Answering Brief in Opposition to BSC's Motion for Summary Judgment of Invalidity of the Asserted Claims of the Palmaz '762 patent, Apr. 21, 2005 (Civil Action No. 03–27–SLR).

The University of Texas Health Science Center at San Antonio Invention Report, Expandable Intraluminal Graft, Julio Cesar Palmaz, Aug. 9, 1984.

Palmaz disclosures prior to Nov. 7, 1984 (e.g., disclosures of 1980 Monograph, 1983 Monograph, and revisions thereof).

Prior use of stents, including neurological applications and Palmaz' implantations (public uses) of stent prior to Nov. 7, 1984.

Various balloon catheters in existence prior to the filing of the '665 patent, including the BlueMax Balloon Dilation Catheters from Medi–Tech, the Trac, the Trac Plus, the Mills Operative Angioplasty, the Mills Operative Coronary Angioplasty, the ACS Low–Profile Steerable Coronary Balloon Dilation Catheter, the Hartzier LPS Coronary Balloon Dilation Catheter, the Simpson Ultra–Low Profile Coronary Balloon Dilation Catheter, (See, e.g., balloon catheters discussed in Blue Max Catheter brochure from 1985/Cook Incorporated Catalog 1982–84, Diagnostic & Interventional Products at 65–66; USCI Division, C.R. Bard, Inc. Hospital Price List (Effective Apr. 15, 1984); "Angioplasty Equipment and Supplies: Technical Considerations" at pp. 93 & 126, from Ch. 7 of the book "Practice of Coronary Angioplasty" (Ischinger, ed. 1986); Topol et al., "Selection of dilation hardware for ptca—1985," *Catherization and Cardiovascular Diagnosis* 11(6): 629–637 (1985)).

Abele, "Balloon Catheters and Transluminal Dilatation: Technical Considerations," AJR 135:901–908 (Nov. 1980).

Percutaneous Transluminal Angioplasty, Ch. 8, pp. 31–36, "Basic Technology of Balloon Catheters," by Abele (1983).

Bernhard, "Higher Balloon Dilatation Pressure in Coronary Angioplasty," *American Heart Journal*, 619–20 (Apr. 1984).

Chuang, "Nonoperative Retrieval of Gianturco Coils from Abdominal Aorta," AJR 132;996–997 (Jun. 1979).

Chuang, "Complications of Coil Embolization: Prevention and Management," AJR 137:809–813 (Oct. 1981).

Coons, H., et al., "Large–Bore, Long Blliary Endoprostheses (Biliary Stents) for Improved Drainage," Radiology 148:89–94 (1983).

Cragg A. et al., Transluminal Expandable Nitinol Coil Stent Grafting, Radiology 147:261–263 (Apr. 1983).

Dotter, "Transluminally Placed Coil–Spring Endarterial Tube Grafts: Long–Term Patency in Canlan Popliteal Artery," *Invest. Radiol.* 4:329–32 (1969).

Dotter et al., "Transluminal Expandable Nitinol Coil Stent Grafting:Preliminary Report," *Radiology* 147:259–260 (Apr. 1983).

Fellows, "Therapeutic Catheter Procedures in Congenital Heart Disease Current Status and Future Prospects," *Cardiovasc Intervent Radiol* 7:170–177 (Jun. 1984).

Glanz et al., "Stenotic Lesions in Dialysis–access Fistulas: Treatment by Translumninal Angioplasty Using High Pressure Balloons," *Radiology*156:236 (Jul. 1985).

Gruntzig, "Technique of Percutaneous Transluminal Angioplasty with the Gruntzig Balloon Catheter," *AJR* 132:547–552 (Apr. 1979).

Gruentzig, "Percutaneous transluminal coronary angioplasty," *Seminarsin Roentgenology*, 16:152–153 (Apr. 1981).

Harries–Jones, E., et al., "Repositioning of Biliary Endoprosthesis with Gruntzig Balloon Catheters," AJR 138:771–772 (1982).

Honickman, S., et al., "Malpositioned Biliary Endoprosthesis: Retrieval Using a Vascular Balloon Catheter," Radiology 144:423–425 (1982).

Kerlan, R. et al., "Biliary Endoprostheses—Insertion Using a Combined Peroral–Transhepatic Method," Radiology 150:828–830 (1984).

Lary et al., "The Experimental Use of Steel Mesh Tubes for the Replacement of Arterial Segments," AMA Archives of Surgery 72:69–75 (Jan. 1956).

Maass et al., "Radiological Follow–up of Transluminally Inserted Vascular Endoprostheses: An Experimental Study Using Expanding Spirals," Radiology 152:659–663 (1984).

Percutaneous Transluminal Angioplasty, Ch. 9, pp. 37–45, "Dilatation and the Expanding Balloon Catheter, Advantages of the Expanding Balloon Catheter," by Olbert et al. (1983).

Program Abstract for the Nov. 1984 Annual Meeting of the Radiological Society of North America: Palmaz et al., "Expandable Intraluminal Graft: A Preliminary Study," (Oct. 1984).

Papanicolaou, N., et al., "Insertion of a Biliary Endoprosthesis Using a Balloon Dilation Catheter," Gastrointestinal Radiology 10:394–396 (1985).

Simpson, "A New Catheter System for Coronary Angioplasty," *The American Journal of Cardiology* at 49:1216–1222 (Apr. 1982).

Teplick et al., "Management of Obstructed Biliary Endoprostheses" CardioVascular and Interventional Radiology 8:164–167 (May 1985).

Wright et al., "Percutaneous Endovascular Stents: An Experimental Evaluation," Radiology 156:69–72 (Jul. 1985).

Prior art cited in the file histories for the '665 patent and its reexamination files.

*Cordis Corp.* v. *Boston Scientific Corp., et al.*, Appeal Brief for Defendants–Cross–Appellants, Court of Appeals for the Federal Circuit, May 12, 2008 (Appeal Nos. 208–1003,–1072).

*Cordis Corporation* v. *Boston Scientific Corp., and Scimed Life Systems, Inc.*, Response and Reply Brief for Plaintiff–Appellant Cordis Corporation, Court of Appeals for the Federal Circuit, Aug. 22, 2008 (Appeal Nos. 2008–1003, –1072).

Civil Action No. 97–550–SLR—*Cordis Corporation* v. *Medtronic Vascular, Inc., et al.*, and Civil Action No. 98–19–SLR—*Boston Scientific Corporation et al.* v. *Ethicon, Inc. et al.*, Memorandum Opinion dated Sep. 15, 2008 (15 pages).

Civil Action No. 97–550–SLR—*Cordis Corporation* v. *Medtronic Vascular, Inc., et al.*, and Civil Action No. 98–19–SLR—*Boston Scientific Corporation et al.* v. *Ethicon, Inc. et al.*, Order dated Sep. 15, 2008 (2 pages).

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–12, 14–23 and 25–59 is confirmed.

Claims 13 and 24 were previously cancelled.

\* \* \* \* \*